(12) United States Patent
Pan et al.

(10) Patent No.: US 7,488,714 B2
(45) Date of Patent: *Feb. 10, 2009

(54) PEPTIDES ACTING AS BOTH GLP-1 RECEPTOR AGONISTS AND GLUCAGON RECEPTOR ANTAGONISTS AND THEIR PHARMACOLOGICAL METHODS OF USE

(75) Inventors: Clark Pan, Castro Valley, CA (US); James Whelan, Madison, CT (US); Kevin B. Clairmont, Chesire, CT (US)

(73) Assignee: Bayer Pharmaceuticals Corporation, West Haven, CT (US)

( * ) Notice: Subject to any disclaimer, the term of this patent is extended or adjusted under 35 U.S.C. 154(b) by 101 days.

This patent is subject to a terminal disclaimer.

(21) Appl. No.: 11/212,439

(22) Filed: Aug. 26, 2005

(65) Prior Publication Data

US 2005/0288248 A1    Dec. 29, 2005

Related U.S. Application Data

(62) Division of application No. 10/265,345, filed on Oct. 3, 2002, now Pat. No. 6,864,069.

(60) Provisional application No. 60/327,730, filed on Oct. 5, 2001.

(51) Int. Cl.
*A61K 38/00* (2006.01)
*A61K 38/28* (2006.01)
*C07K 2/00* (2006.01)

(52) U.S. Cl. .......... 514/12; 514/2; 514/3; 530/300; 530/303; 530/308; 530/324

(58) Field of Classification Search .......... None
See application file for complete search history.

(56) References Cited

U.S. PATENT DOCUMENTS 6,232,310 B1    5/2001 Hansen et al. .......... 514/224.2
7,041,646 B2 *  5/2006 Pan et al. .................. 514/12

FOREIGN PATENT DOCUMENTS

WO    9111457    8/1991

OTHER PUBLICATIONS

Claus et al . J Endocrinol. 192(2):371-80, 2007.*
Pan et al J Biol Chem. 281(18):12506-15, 2006.*
Frezza et al, Dig Dis Sci. 52:643-649, 2007.*
Combettes, Curr Opin Pharmacol. (6):598-605. 2006.*
Bojanowska Med Sci Monit. 2005 (8):RA271-278, 2005.*

* cited by examiner

*Primary Examiner*—Sumesh Kaushal
(74) *Attorney, Agent, or Firm*—Edwards Angell Palmer & Dodge LLP; Ralph Loren; Barry Kramer

(57) ABSTRACT

The invention provides polypeptides that act both as an agonist of the GLP-1 receptor and an antagonist of the glucagon receptor. Such polypeptides are useful for treating individuals with type 2 diabetes or other metabolic disorders.

9 Claims, 1 Drawing Sheet

PEPTIDES ACTING AS BOTH GLP-1 RECEPTOR AGONISTS AND GLUCAGON RECEPTOR ANTAGONISTS AND THEIR PHARMACOLOGICAL METHODS OF USE

This application is a divisional application of U.S. Ser. No. 10/265,345, filed Oct. 3, 2002, now U.S. Pat. No. 6,864,069.

FIELD OF THE INVENTION

This invention relates to newly identified polypeptides that act both as an agonist of the GLP-1 receptor and an antagonist of the glucagon receptor and the use of such polypeptides for therapeutic purposes. More particularly, polypeptides of the present invention are useful in stimulating the release of insulin from pancreatic beta cells in a glucose-dependent manner and reducing glucagon-mediated secretion of glucose from the liver, thereby providing a treatment option for those individuals afflicted with a metabolic disorder such as diabetes, hyperglycemia, impaired fasting glucose, impaired glucose tolerance, prediabetic states, and obesity.

BACKGROUND OF THE RELATED ART

Diabetes is characterized by impaired insulin secretion manifesting itself among other things by an elevated blood glucose level in the diabetic patient. Underlying defects lead to a classification of diabetes into two major groups: type I diabetes (or insulin dependent diabetes mellitus, IDDM), which arises when patients lack insulin-producing beta-cells in their pancreatic glands, and type 2 diabetes (or non-insulin dependent diabetes mellitus, NIDDM), which occurs in patients with an impaired beta-cell insulin secretion and/or alterations in insulin action.

Type 1 diabetic patients are currently treated with insulin, while the majority of type 2 diabetic patients can be treated with agents that stimulate beta-cell function or with agents that enhance the tissue sensitivity of the patients towards insulin. Over time, almost one-half of type 2 diabetic subjects lose their response to these agents and then must be placed on insulin therapy. The drugs presently used to treat type 2 diabetes include alpha-glucosidase inhibitors (PRECOSE®, VOGLIBOSE™, and MIGLITOL®), insulin sensitizers (e.g., Avandia™, ActoS™ and Rezulin™), insulin secretagogues (sulfonylureas ("SFUs") and other agents that act by the ATP-dependent K⁺ channel), and GLUCOPHAGE™ (metformin HCl).

Alpha-glucosidase inhibitors. Alpha-glucosidase inhibitors reduce the excursion of postprandial glucose by delaying the absorption of glucose from the gut. These drugs are safe and provide treatment for mild to moderately affected diabetic subjects. However, gastrointestinal side effects have been reported in the literature and limit their effectiveness.

Insulin sensitizers. Insulin sensitizers are drugs that enhance the body's response to insulin. Thiozolidinediones such as Avandia™ (rosiglitazone) and Actos™ activate peroxisome proliferator-activated receptor (PPAR) gamma and modulate the activity of a set of genes that have not been well described. Hepatic effects (e.g., drug induced hepatotoxicity and elevated liver enzyme levels) do not appear to be a significant problem in patients using Avandia™ and Actos™. Even so, liver enzyme testing is recommended every two months in the first year of therapy and periodically thereafter. Avandia™ and Actos™ treatments are associated with fluid retention, edema, and weight gain. Avandia™ is not indicated for use with insulin because of concern about congestive heart failure. Rezulin™ (troglitazone), the first drug in this class, was withdrawn because of elevated liver enzyme levels and drug-induced hepatotoxicity.

Insulin secretagogues. Sulfonylureas (SFUs) and the non-sulfonylureas, Nateglinide and Pepaglinide act through the ATP-dependent potassium channel to cause glucose-independent insulin secretion. These drugs are standard therapy for type 2 diabetics that have mild to moderate fasting hyperglycemia. The insulin secretagogues have limitations that include a potential for inducing hypoglycemia, weight gain, and high primary and secondary failure rates. Ten to 20% of initially treated patients fail to show a significant treatment effect (primary failure). Secondary failure is demonstrated by an additional 20-30% loss of treatment effect after six months of treatment with insulin secretagogues. Insulin treatment is required in 50% of the insulin secretagogues responders after 5-7 years of therapy (Scheen et al., *Diabetes Res. Clin. Pract.* 6:533-543, 1989). Nateglinide and Pepaglinide are short-acting drugs that need to be taken three times a day. They are used only for the control of post-prandial glucose and not for control of fasting glucose.

GLUCOPHAGE™ is a biguanide that lowers blood glucose by decreasing hepatic glucose output and increasing peripheral glucose uptake and utilization. The drug is effective at lowering blood glucose in mildly and moderately affected subjects and does not have a side effect of weight gain or a potential to induce hypoglycemia. However, GLUCOPHAGE™ has a number of side effects, including gastrointestinal disturbances and lactic acidosis. GLUCOPHAGE™ is contraindicated in diabetics over the age of 70 and in subjects with impaired renal or liver function. Finally, GLUCOPHAGE™ has the same primary and secondary failure rates as the insulin secretagogues.

Insulin treatment is instituted after diet, exercise, and oral medications have failed to control blood glucose adequately. This treatment has several drawbacks: it is an injectable, it can produce hypoglycemia, and it can cause weight gain. The possibility of inducing hypoglycemia with insulin limits the extent that hypoglycemia can be controlled.

Problems with current treatments necessitate new therapies to treat type 2 diabetes. In particular, new treatments to retain normal (i.e., glucose-dependent) insulin secretion are needed. Given glucagon-like peptide-1's ("GLP-1") role in promoting glucose-regulated insulin secretion in the pancreas, GLP-1 receptor agonists are potentially valuable in the treatment of such diseases. Moreover, glucagon receptor antagonists should prove valuable in treating type 2 diabetes given glucagon's role in elevating plasma glucose by stimulating hepatic glycogenolysis and gluconeogenesis.

GLP-1 and glucagon are members of a family of structurally related peptide hormones, the glucagon/secretin family. Within this family, GLP-1(7-36) and GLP-1(7-37) (30 amino acids and 31 amino acids, respectively) and glucagon (30 amino acids) constitute a highly homologous set of peptides. In addition, these two hormones originate from a common precursor, preproglucagon which, upon tissue-specific processing, leads to production of GLP-1 predominantly in the intestine and glucagon in the pancreas. The receptors for these two peptides are homologous (58% identity) and belong to the family of G-protein coupled receptors.

GLP-1 and glucagon both play major roles in overall glucose homeostasis. GLP-1 lowers plasma glucose concentrations mediated by glucose dependent insulin secretion, whereas glucagon increases plasma glucose concentrations. Given the important roles of both GLP-1 and glucagon in maintaining normal blood glucose concentrations, there has been considerable interest in the identification of GLP-1 receptor agonists and glucagon receptor antagonists. Clinical studies have demonstrated the ability of GLP-1 infusion to promote insulin secretion and to normalize plasma glucose in diabetic subjects. However, GLP-1 is rapidly degraded and has a very short half-life in the body. Furthermore, GLP-1 causes gut motility side effects at or near its therapeutic doses. Therefore, GLP-1 itself has significant limitations as a therapeutic agent, and modified versions of the peptide with enhanced stability are being pursued. Non-peptide agonists of the GLP-1 receptor have not been described to date.

Peptide analogs of glucagon have been identified which act as glucagon antagonists and reduce hyperglycemia in diabetic rats. However, no peptide glucagon antagonist has moved beyond preclincal development. A number of structurally diverse non-peptide glucagon receptor antagonists have been reported in the scientific and patent literature. However, attempts to identify small molecule inhibitors of the glucagon receptor have met with limited success in vivo. The only antagonist of glucagon action known to be active in a clinical study is a compound identified as BAY 27-9955. A potential side effect of glucagon antagonism is hypoglycemia.

Because of the potential side effects associated with administering either a GLP-1 receptor agonist or a glucagon receptor antagonist alone, a combination therapy would have an advantage of maintaining the desired lowering of blood glucose while reducing the side effects. Co-administration, however, requires a single formulation and delivery approach that yields appropriate pharmokinetic profiles for both peptides. This could be a major obstacle to the development of such a therapeutic.

Based on the foregoing, considerable potential exists for a single therapeutic peptide functioning as both a GLP-1 agonist and a glucagon antagonist in vivo.

SUMMARY OF THE INVENTION

This invention provides novel polypeptides that function both as an agonist of the GLP-1 receptor and antagonist of the glucagon receptor and which are effective in the treatment of diseases and conditions that can be ameliorated by agents having both GLP-1 receptor agonist and glucagon receptor antagonist activity. Polypeptides of the present invention provide a new therapy for patients with, for example, metabolic disorders, such as those resulting from decreased endogenous insulin secretion, in particular type 2 diabetics, or for patients with impaired glucose tolerance, a prediabetic state that has a mild alteration in insulin secretion or impaired fasting glucose, or obesity.

One aspect of the invention is a polypeptide selected from the group consisting of SEQ ID NOS:6-32, as well as fragments, derivatives and variants of polypeptides that function as both an agonist of the GLP-1 receptor and an antagonist of the glucagon receptor at substantially the same level as the polypeptides shown in SEQ ID NOS:6-32 (collectively, "polypeptides of the invention").

Other embodiments of the invention include polynucleotides that encode polypeptides of the invention and the attendant vectors and host cells necessary to recombinantly express the polypeptides.

Still other embodiments of the invention provide methods of treating diabetes and/or other diseases or conditions affected by polypeptides of the invention in mammals, including humans. The methods involve administering a therapeutically effective amount of any of the polypeptides of the present invention to a mammal.

The invention also provides recombinant and synthetic methods of making polypeptides of the invention.

DETAILED DESCRIPTION OF THE PREFERRED EMBODIMENTS

Figure 1:
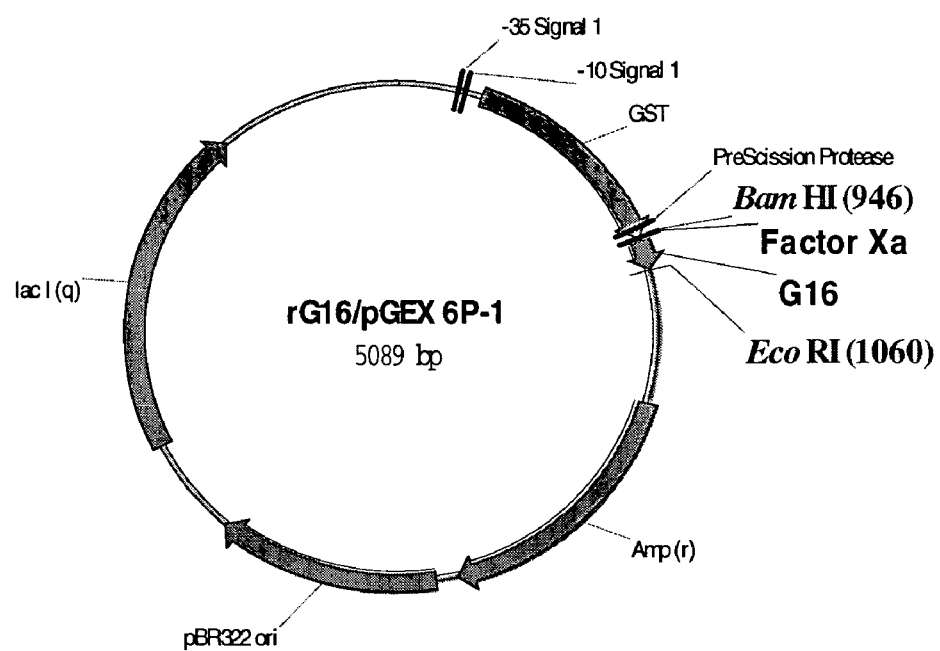
FIG. 1 is a restriction map of a typical plasmid containing a GST-peptide fusion polynucleotide coding sequence.

The invention provides novel polypeptides, as well as fragments, derivatives variants, and analogs thereof that function as both an agonist of the GLP-1 receptor and an antagonist of the glucagon receptor. Polypeptides of the invention function in vivo as both GLP-1 receptor agonists and glucagon receptor antagonists in the prevention and/or treatment of such diseases or conditions as diabetes, hyperglycemia, impaired glucose intolerance, impaired fasting glucose, and obesity.

GLP-1 and glucagon are members of a family of structurally related peptide hormones, the glucagon/secretin family. The stacking alignment below shows the primary structural relationships:

```
Glucagon       HSQGTFTSDYSKYLEGQAAKEFIAWLVKGR     (SEQ ID NO:1)
GLP-1 (7-36)   HAEGTFTSDVSSYLEGQAAKEFIAWLVKGR-NH2 (SEQ ID NO:2)
GLP-1 (7-37)   HAEGTFTSDVSSYLEGQAAKEFIAWLVKGRG    (SEQ ID NO:3)
```

Single-letter abbreviations for amino acids can be found in Zubay, Biochemistry 2d ed., 1988, MacMillan Publishing, New York, p. 33. These polypeptides play a role in overall glucose homeostasis: GLP-1 lowers plasma glucose concentrations, whereas glucagon increases plasma glucose concentrations.

Given GLP-1's role in promoting glucose-regulated insulin secretion in the pancreas, GLP-1 receptor agonists are potentially valuable in the treatment of metabolic disorders and other diseases. Moreover, glucagon receptor antagonists should also prove valuable in treating disease given glucagon's role in elevating plasma glucose by stimulating hepatic glycogenolysis and gluconeogenesis. However, these facts alone do not guarantee glucose reduction in vivo without inducing significant side effects.

The invention provides new polypeptides that are both GLP-1 receptor agonists and glucagon receptor antagonists. Without being bound to theory, we believe that polypeptides of the invention are capable of reducing glucose levels in vivo by stimulating insulin release from pancreatic beta cells in a glucose-dependent manner, while at the same time reducing glucagon-mediated secretion of glucose from the liver.

GLP-1 Receptor Agonist and Glucagon Receptor Antagonist Polypeptides

Polypeptides of the invention function both as a GLP-1 receptor agonist and a glucagon receptor antagonist. The GLP-1 receptor agonist component of such polypeptides activates the GLP-1 receptor in one or more in vitro or in vivo assays for GLP-1 receptor activation. Examples of such assays include, but are not limited to, in vitro assays for induction of cAMP in RINm5F cells, in vitro assays for induction of insulin secretion from pancreatic β-cells, in vivo assays for reduction in plasma glucose levels, and in vivo assays for elevation in plasma insulin levels as described in the specific examples below.

Polypeptides of the invention also demonstrate glucagon receptor antagonist activity in one or more in vitro or in vivo assays for inhibition of glucagon receptor activation. Examples of such assays include, but are not limited to, in vitro assays to measure inhibition of glucagon-mediated increase in cellular cAMP, in vitro assays to measure inhibition of glucagon-mediated glucose release from, for example, cultured hepatocytes, or in vivo assays for glucagon stimulated glucose production as described in the specific examples below.

Preferred polypeptides of the invention are selected from the group consisting of (1) SEQ ID NOS:6-32 and (2) fragments, derivatives, variants, and analogs thereof that function as both an agonist of the GLP-1 receptor and an antagonist of the glucagon receptor at substantially the same level as any of the polypeptides shown in SEQ ID NOS:6-32.

Polypeptides of the present invention may be naturally-occurring polypeptides, recombinant polypeptides, or synthetic polypeptides.

Fragments, Derivatives, Variants, and Analogs

Fragment, derivative, variant, and analog polypeptides retain substantially the same biological function or activity as, for example, polypeptides shown in SEQ ID NOS:6-32. "Substantially the same biological function or activity" is about 30% to 100% (i.e., 30, 40, 50, 60, 70, 80, 90, or 100%) or more of the same biological activity of the full-length polypeptide to which it is compared.

Derivatives

Derivatives include polypeptides of the invention that have been chemically modified to provide an additional structure and/or function. For example, polyethylene glycol (PEG) or a fatty acid can be added to a polypeptide to improve its half-life. Fusion polypeptides which confer targeting specificity or an additional activity also can be constructed, as described in more detail below.

Derivatives can be modified by either a natural process, such as posttranslational processing, or by chemical modification techniques, both of which are well known in the art. Modifications can occur anywhere in a polypeptide, including the peptide backbone, the amino acid side-chains, and the amino or carboxyl termini. It will be appreciated that the same type of modification may be present to the same or varying degrees at several sites in a given polypeptide. Also, a variant may contain one or more different types of modifications. Polypeptides may be branched, for example, as a result of ubiquitination, and they may be cyclic, with or without branching.

Other chemical modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formulation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, T. E. Creighton, PROTEINS, STRUCTURE AND MOLECULAR PROPERTIES, 2nd ed., W.H. Freeman and Company, New York (1993); POSTTRANSLATIONAL COVALENT MODIFICATION OF PROTEINS, B. C. Johnson, ed., Academic Press, New York, pgs. 1-12 (1983); Seifter et al., Meth. Enzymol 182:626-46 (1990); Rattan et al., Ann. N.Y. Acad. Sci. 663:48-62, 1992).

Derivatives also include mature polypeptides that have been fused with another polypeptide, such as for example human serum albumin, to improve their pharmacokinetic profile. Fusion of two polypeptides can be accomplished by any means known to one skilled in the art. For example, a DNA encoding human serum albumin and a DNA sequence encoding a polypeptide of the invention can be cloned into any mammalian expression vector known to one skilled in the art. Location of a polypeptide of the invention N-terminal to the other polypeptide is preferred, because it appears that a free N-terminal histidine is required for GLP-1 receptor activity (Kawa, Endocrinology April; 124(49):1768-73, 1989). The resulting recombinant fusion protein can then be expressed by transforming a suitable cell line, such as HKB or CHO, with the vector and expressing the fusion protein.

Preferred derivatives include polypeptides of the invention (SEQ ID NOS:6-32) to which a PEG moiety or a fatty acid moiety has been attached. The PEG moiety can be, for example, a PEG with a molecular weight greater than 22 kDa, preferably a molecular weight of between 25 kDa and 100 kDa (e.g., 25, 30, 35, 40, 50, 55, 60, 65, 70, 75, 80, 85, 90, 95 or 100 kDa), and more preferably a molecular weight of between 35 kDa and 45 kDa (e.g., 35, 36, 37, 38, 39, 40, 41, 42, 43, 44, or 45 kDa). Examples of such PEGylated polypeptides are those that contain a 22 kDa PEG moiety attached to the cysteine residue at position 31 of SEQ ID NOS:19 or 25. See SEQ ID NOS:20 and 26 and Table 2. Alternatively, a 43 kDa PEG moiety can be attached to the cysteine residue at position 31 of SEQ ID NO:25. See SEQ ID NO:27 and Table 2. A PEG moiety can be added to a cysteine residue of polypeptides of the invention by methods well known in the art, for example, see Example 19.

Other preferred derivatives have a fatty acid moiety attached to the polypeptide. The fatty acid moiety can be, for example, a fatty acid between $C_{12}$ and $C_{20}$, preferably $C_{14}$ and $C_{18}$, and most preferably a $C_{16}$ fatty acid. Examples of such polypeptides are SEQ ID NOS:28-32, which contain a $C_{16}$ (palmitate) fatty acid moiety attached to a lysine residue within the peptide. See Table 2. A fatty acid moiety can be added to a lysine residue of polypeptides of the invention by methods well known in the art, for example, fatty acid acylation (Knudsen et al., J. Med. Chem. 43:1664-1669, 2000).

Variants

Variants are polypeptides on the invention that have or more amino acid sequence changes with respect to the amino acid sequences shown in SEQ ID NOS:6-32. Variants also can have amino acids joined to each other by modified peptide bonds, i.e., peptide isosteres, and may contain amino acids other than the 20 naturally occurring amino acids.

Preferably, variants contain one or more conservative amino acid substitutions (i.e., 1, 2, 3, 4, 5, 6, 7, 8, 9, or 10 substitutions), preferably at nonessential amino acid residues. A "nonessential" amino acid residue is a residue that can be altered from a wild-type sequence of a protein without altering its biological activity, whereas an "essential" amino acid residue is required for biological activity. A conservative amino acid substitution is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Non-conservative substitutions would not be made for conserved amino acid residues or for amino acid residues residing within a conserved protein domain.

Conservative amino acid substitutions are preferably at positions 11, 12, 16, 17, or 18 of the consensus polypeptide shown SEQ ID NO:34. Position 11 preferably is R, S, A, K, G, or T and more preferably R, A, G, or S. Position 12 preferably is K, N, R, H, A, S or Q and more preferably K, A, S, or N. Position 16 preferably is K, R, V, I, L, M, F, W, Y, A, S, T, N, Q, G, or H, and more preferably K, V, I, F, A, S, or N. Position 17 preferably is D, E, H, K, R, F, I, L, M, Y, V, W, A, S, T, N, Q, or G, and more preferably R, A, L, M, V, S, H, E, or Q. Position 18 preferably is K, R, F, I, L, Y, V, M, A, G, or H and more preferably K, R, F, I, L, Y or A. All possible combinations of substitutions at positions 11, 12, 16, 17, and 18, including no substitution at any one, two, three, or four of these positions, are specifically envisioned.

Variants also include polypeptides that differ in amino acid sequence due to mutagenesis. Variants that function as both GLP-1 receptor agonists and glucagon receptor antagonists can be identified by screening combinatorial libraries of mutants, for example, mutants of polypeptides with conservative substitutions at 1 or more positions (i.e., at 1, 2, 3, 4, 5, 6, 7, 8, 9, or 10 positions) can be screened for GLP-1 receptor agonist activity and glucagon receptor antagonist activity using methods well known in the art and described in the specific examples below.

Analogs

An analog includes a propolypeptide, wherein the propolypeptide includes an amino acid sequence of a polypeptide of the invention. Active polypeptides of the invention can be cleaved from the additional amino acids in the propolypeptide molecule by natural, in vivo processes or by procedures well known in the art, such as by enzymatic or chemical cleavage.

Fragments

A fragment is less than a full-length polypeptide of the invention, including a full-length derivative, variant, or analog, which has GLP-1 receptor agonist and glucagon receptor antagonist activity.

Polynucleotides

Any polynucleotide sequence that encodes a polypeptide of the invention can be used to express the polypeptide. Polynucleotides can consist only of a coding sequence for a polypeptide or can include additional coding and/or non-coding sequences.

Polynucleotide sequences encoding a polypeptide of the invention can be synthesized in whole or in part using chemical methods well known in the art (see, for example, Caruthers et al., *Nucl. Acids Res. Symp. Ser.* 215-23, 1980; Horn et al., *Nucl. Acids Res. Symp. Ser.* 225-32, 1980). The polynucleotide that encodes the polypeptide can then be cloned into an expression vector to express the polypeptide or into a cloning vector, to propagate the polynucleotide.

As will be understood by those of skill in the art, it may be advantageous to produce the polypeptide-encoding nucleotide sequences possessing non-naturally occurring codons. For example, codons preferred by a particular prokaryotic or eukaryotic host can be selected to increase the rate of polypeptide expression or to produce an RNA transcript having desirable properties, such as a half-life, which is longer than that of a transcript generated from the naturally occurring sequence.

The nucleotide sequences disclosed herein can be engineered using methods generally known in the art to alter the polypeptide-encoding sequences for a variety of reasons, including but not limited to, alterations which modify the cloning, processing, and/or expression of the polypeptide or mRNA product. DNA shuffling by random fragmentation and PCR reassembly of gene fragments and synthetic oligonucleotides can be used to engineer the nucleotide sequences. For example, site-directed mutagenesis can be used to insert new restriction sites, alter glycosylation patterns, change codon preference, produce splice variants, introduce mutations, and so forth.

Vectors

The present invention also includes cloning and expression vectors comprising one or more nucleotide sequences encoding a polypeptide of the invention. The nucleotide sequence can be inserted in a forward or reverse orientation. A DNA sequence may be inserted into a vector by a variety of procedures. In general, a DNA sequence is inserted into an appropriate restriction endonuclease site by procedures known in the art and described in Sambrook et al., MOLECULAR CLONING: A LABORATORY MANUAL, 2d ed., (Cold Spring Harbor, N.Y., 1989). Such procedures and others are deemed to be within the scope of those skilled in the art.

Examples of cloning vectors include, but are not limited to pBR322, pUC18, pUC19, pSport, and pCRII.

In a preferred aspect of this embodiment, an expression vector further comprises regulatory sequences, including, for example, a promoter, operably linked to the coding sequence. Large numbers of suitable expression vectors and promoters are known to those of skill in the art and are commercially available. The following expression vectors are provided by way of example. Bacterial expression vectors include, but are not limited to, pQE70, pQE60, pQE-9 (Qiagen), pBS, phagescript, psiX174, pBluescript SK, pBsKS, pNH8a, pNH16a, pNH18a, pNH46a (Stratagene); pTRC99A, pKK223-3, pKK233-3, pDR540, PRIT5 (Pharmacia). Eukaryotic expression vectors include, but are not limited to, pWLneo, pSV2cat, pOG44, pXT1, pSG (Stratagene) pSVK3, pBPV, pMSG, PSVL (Pharmacia). However, any other cloning or expression vector may be used as long as it is replicable and viable in the desired host. Promoter regions can be selected from any desired gene using CAT (chloramphenicol transferase) expression vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of an appropriate vector and promoter is well within the level of ordinary skill in the art.

An expression vector also can contain a ribosome binding site for translation initiation, a transcription terminator, and appropriate sequences for amplifying expression. Expression vectors can contain a gene to provide a phenotypic trait for selection of transformed host cells, such as dihydrofolate reductase or neomycin resistance for a eukaryotic cell culture, or such as tetracycline or ampicillin resistance for culture in *E. coli*.

Libraries

In one embodiment, a library of variants is generated by combinatorial mutagenesis at the nucleic acid level and is encoded by a variegated gene library. A library of variants can be produced, for example, by enzymatically ligating a mixture of synthetic oligonucleotides into gene sequences such that a degenerate set of potential variant amino acid sequences is expressible as individual polypeptides or, alternatively, as a set of larger fusion proteins (for example, for phage display) containing the set of sequences therein.

There are a variety of methods that can be used to produce libraries of potential variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential analog sequences. Methods for synthesizing degenerate oligonucleotides are known in the art (see, e.g., Narang, Tetrahedron 39:3 (1983); Itakura et al., Annu. Rev. Biochem. 53:323 (1984); Itakura et al., Science 198:1056 (1984); Ike et al., Nucleic Acid Res. 11:477, 1983).

Several techniques are known in the art for screening gene products of combinatorial libraries made by point mutations or truncation and for screening cDNA libraries for gene products having a selected property. Such techniques are adaptable for rapid screening of the gene libraries generated by the combinatorial mutagenesis of polypeptides of the invention. The most widely used techniques, which are amenable to high through-put analysis for screening large gene libraries, typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique that enhances the frequency of functional mutants in the libraries, can be used in combination with the screening assays to identify the desired variants.

Host Cells

The present invention also provides host cells containing the above-described vectors. The host cell can be a higher eukaryotic cell, such as a mammalian cell, or a lower eukaryotic cell, such as a yeast cell. Alternatively, the host cell can be a prokaryotic cell, such as a bacterial cell.

Host cells can be genetically engineered (transduced, transformed or transfected) with cloning or expression vectors of the invention. The vector may be, for example, in the form of a plasmid, a viral particle, or a phage. Engineered host cells can be cultured in conventional nutrient media modified as appropriate for activating promoters or selecting transformants. The selection of appropriate culture conditions, such as temperature and pH, are well within the skill of the ordinarily skilled artisan.

As representative examples of appropriate hosts, include, but are not limited to, bacterial cells, such as E. coli, Salmonella typhimurium, Streptomyces; fungal cells, such as yeast; insect cells, such as Drosophila S2 and Spodoptera Sf9; mammalian cells such as CHO, COS or Bowes melanoma. The selection of an appropriate host is deemed to be within the scope of those skilled in the art from the teachings herein.

Introduction of the construct into the host cell can be effected, for example, by calcium phosphate transfection, DEAE-Dextran mediated transfection, or electroporation (Davis et al., BASIC METHODS IN MOLECULAR BIOLOGY, 1986). Constructs in host cells can be used in a conventional manner to produce the gene product encoded by the recombinant sequence.

Protein Expression

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described above and in Sambrook et al., MOLECULAR CLONING: A LABORATORY MANUAL, 2d ed., (Cold Spring Harbor, N.Y., 1989).

Transcription of a DNA encoding polypeptides of the present invention by higher eukaryotes can be increased by inserting an enhancer sequence into the expression vector. Enhancers are cis-acting elements of DNA, usually from about 10 to 300 bp, that act on a promoter to increase its transcription. Examples include the SV40 enhancer on the late side of the replication origin (bp 100 to 270), a cytomegalovirus early promoter enhancer, a polyoma enhancer on the late side of the replication origin, and adenovirus enhancers. Generally, recombinant expression vectors will include origins of replication and selectable markers permitting transformation of the host cell, e.g., the ampicillin resistance gene of E. coli and S. cerevisiae TRP1 gene, and a promoter derived from a highly expressed gene to direct transcription of a downstream structural sequence. Such promoters can be derived from operons encoding glycolytic enzymes such as 3-phosphoglycerate kinase (PGK), α factor, acid phosphatase, or heat shock proteins, among others. The heterologous structural sequence is assembled in appropriate phase with translation, initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

After transformation of a suitable host strain and growth of the host strain to an appropriate cell density, the selected promoter is derepressed by appropriate means (e.g., temperature shift or chemical induction), and cells are cultured for an additional period. Cells are typically harvested by centrifugation and disrupted by physical or chemical means. The resulting crude extract is retained for further purification. Microbial cells employed in expression of proteins can be disrupted by any convenient method, including freeze-thaw cycling, sonication, mechanical disruption, or use of cell lysing agents.

Various mammalian cell culture systems also can be employed to express recombinant protein. Examples of mammalian expression systems include the COS-7 lines of monkey kidney fibroblasts, described by Gluzman, Cell 23:175 (1981), and other cell lines capable of expressing a compatible vector, for example, C127, 3T3, CHO, HeLa and HBK cell lines.

Protein Purification

Polypeptides of the present invention may be recovered and purified from recombinant cell cultures by methods well known in the art, including ammonium sulfate or ethanol precipitation, acid extraction, anion or cation exchange chromatography, phosphocellulose chromatography, hydrophobic interaction chromatography, affinity chromatography, hydroxyapatite chromatography, and lectin chromatography.

High performance liquid chromatography (HPLC) can be employed as a final purification step.

Polypeptides of the invention can be conveniently isolated as described in the specific examples below. A purified polypeptide is at least about 70% pure, that is, the isolated polypeptide is substantially free of cellular material and has less than about 30% (by dry weight) of non-polypeptide material. Preferably, the preparations are 85% through 99% (i.e., 85, 87, 89, 91, 93, 95, 96, 97, 98, and 99%) pure. Purity of the preparations can be assessed by any means known in the art, such as SDS-polyacrylamide gel electrophoresis, mass spectroscopy and liquid chromatography.

Post-Translational Modification

Depending upon the host employed in a recombinant production procedure, polypeptides of the invention may be glycosylated with mammalian or other eukaryotic carbohydrates or may be non-glycosylated. Polypeptides of the invention may also include an initial methionine amino acid residue.

Chemical Synthesis

Alternatively, polypeptides of the invention can be produced using chemical methods to synthesize its amino acid sequence, such as by direct peptide synthesis using solid-phase techniques (see, for example, Merrifield, *J. Am. Chem. Soc.* 85, 2149-2154, 1963; Roberge et al, *Science* 269, 202-204, 1995). Polypeptide synthesis can be performed using manual techniques or by automation. Automated synthesis can be achieved, for example, using Applied Biosystems 431A Peptide Synthesizer (Perkin Elmer). Optionally, fragments of a polypeptide can be separately synthesized and combined using chemical methods to produce a full-length molecule.

A newly synthesized polypeptide can be substantially purified by preparative high performance liquid chromatography (see, for example, Creighton, Proteins: Structures And Molecular Principles, WH Freeman and Co., New York, N.Y., 1983). The composition of a synthetic polypeptide of the present invention can be confirmed by amino acid analysis or sequencing by, for example, the Edman degradation procedure (see, Creighton, supra). Additionally, any portion of the amino acid sequence of the polypeptide can be altered during direct synthesis and/or combined using chemical methods with sequences from other proteins to produce a variant polypeptide or a fusion polypeptide.

Pharmaceutical Applications

Polypeptides of the present invention can be used to treat type 2 diabetes (non-insulin dependent diabetes mellitus) and/or to prevent subjects with impaired glucose tolerance, impaired fasting glucose, hypoglycemia, and/or obesity from developing type 2 diabetes.

Pharmaceutical Compositions

Polypeptides of the present invention may be combined with a suitable pharmaceutical carrier to form a pharmaceutical composition for parenteral administration. Such compositions comprise a therapeutically effective amount of the polypeptide and a pharmaceutically acceptable carrier or excipient. Pharmaceutically acceptable carriers, include but are not limited to, saline, buffered saline, dextrose, water, glycerol, ethanol, and combinations thereof. The formulation should suit the mode of administration.

Pharmaceutical compositions may be administered in a convenient manner, e.g., by oral, topical, intravenous, intraperitoneal, intramuscular, subcutaneous, intranasal, or intradermal routes. Pharmaceutical compositions are administered in an amount, that is effective for treating and/or prophylaxis of the specific indication. Suitable doses range from at least about 3.5 ng of active polypeptide (i.e., not including the weight of a PEG or fatty acid moiety)/kg body weight to about 100 μg/kg body weight per day. In most cases, the dosage is from about 0.1 μg/kg to about 35 μg/kg (i.e., 0.1, 1, 5, 10, 15, 20, 25, 30, and 35 μg/kg) body weight daily, taking into account the routes of administration, symptoms, etc. These numbers do not take into account the bioavailability of the peptide in vivo, in which case more or less may be used to attain the effective dose desired. Determination of a dose is well within the skill of the ordinary artisan and requires only routine screening.

Polypeptides of the present invention may also be employed in combination with other pharmaceutical agents useful in the treatment of diabetes, impaired fasting glucose, impaired glucose tolerance, hyperglycemia, and obesity. Suitable agents include insulin secretagogues, insulin sensitizers, and metformin HCl.

Kits

The invention also provides pharmaceutical packs or kits comprising one or more containers filled with one or more of the ingredients of pharmaceutical compositions of the invention. A notice in a form prescribed by a governmental agency that regulates the manufacture, use or sale of pharmaceuticals or biological products and reflecting approval by the agency can be associated with the pack or kit.

Gene Therapy

A polypeptide of the invention may also be expressed in vivo, which is often referred to as "gene therapy." Thus, for example, cells may be engineered with a polynucleotide (DNA or RNA) encoding for the polypeptide ex vivo and the engineered cells then provided to a patient to be treated with the polypeptide. Such methods are well known in the art. For example, cells may be engineered by procedures known in the art by use of a retroviral particle containing RNA encoding for polypeptides of the present invention.

In a preferred embodiment, the DNA encoding the polypeptides of the invention is used in gene therapy for disorders such as diabetes. According to this embodiment, gene therapy with DNA encoding polypeptides of the invention is provided to a patient in need thereof, concurrent with, or immediately after diagnosis.

Local delivery of polypeptides using gene therapy may provide the therapeutic agent to the target area, i.e., the pancreas. For instance a pancreas-specific promoter was used to create a beta-cell pancreatic tumor mouse model (Hanahan, *Nature* 315(6015):115-22, 1985).

Both in vitro and in vivo gene therapy methodologies are contemplated. Several methods for transferring potentially therapeutic genes to defined cell populations are known. See, e.g., Mulligan, *Science* 260: 926-31, 1993. These methods include:

1) Direct gene transfer. See, e.g., Wolff et al., "Direct Gene transfer Into Mouse Muscle In Vivo," *Science* 247:1465-68, 1990;

2) Liposome-mediated DNA transfer. See, e.g., Caplen et al., "Liposome-mediated CFTR Gene Transfer To The Nasal Epithelium Of Patients With Cystic Fibrosis," *Nature Med.* 3: 39-46, 1995; Crystal, "The Gene As A Drug," *Nature Med.* 1:15-17, 1995; Gao and Huang, "A Novel Cationic Liposome Reagent For Efficient Transfection Of Mammalian Cells," *Biochem. Biophys. Res. Comm.* 179:280-85, 1991;

3) Retrovirus-mediated DNA transfer. See, e.g., Kay et al., "In Vivo Gene Therapy Of Hemophilia B: Sustained Partial Correction In Factor IX-Deficient Dogs," *Science* 262:117-19, 1993; Anderson, "Human Gene Therapy," *Science* 256:808-13, 1992.

4) DNA Virus-mediated DNA transfer. Such DNA viruses include adenoviruses (preferably Ad-2 or Ad-5 based vectors), herpes viruses (preferably herpes simplex virus based vectors), and parvoviruses (preferably "defective" or non-autonomous parvovirus based vectors, more preferably adeno-associated virus based vectors, most preferably AAV-2 based vectors). See, e.g., Ali et al., "The Use Of DNA Viruses As Vectors For Gene Therapy," *Gene Therapy* 1:367-84,1994; U.S. Pat. No. 4,797,368, and U.S. Pat. No. 5,139,941.

Gene Therapy Vector Systems

The choice of a particular vector system for transferring a gene of interest will depend on a variety of factors. One important factor is the nature of the target cell population. Although retroviral vectors have been extensively studied and used in a number of gene therapy applications, these vectors are generally unsuited for infecting non-dividing cells. In addition, retroviruses have the potential for oncogenicity. However, recent developments in the field of lentiviral vectors may circumvent some of these limitations. See Naldini et al., *Science* 272:263-7, 1996.

The skilled artisan will appreciate that any suitable gene therapy vector encoding polypeptides of the invention can be used in accordance with this embodiment. The techniques for constructing such vectors are known. See, e.g., Anderson, *Nature* 392 25-30, 1998; Verma and Somia, *Nature* 389 239-242, 1998. Introduction of the vector to the target site may be accomplished using known techniques.

Suitable gene therapy vectors include one or more promoters. Suitable promoters which may be used include, but are not limited to, viral promoters (e.g., retroviral LTR, SV40 promoter, adenovirus major late promoter, respiratory syncytial virus promoter, B19 parvovirus promoter, and human cytomegalovirus (CMV) promoter described in Miller et al., *Biotechniques* 7(9): 980-990, 1989), cellular promoters (e.g., histone, pol III, and β-actin promoters), and inducible promoters (e.g., MMT promoter, metallothionein promoter, and heat shock promoter). The selection of a suitable promoter will be apparent to those skilled in the art from the teachings contained herein.

Retroviruses

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, Myeloproliferative Sarcoma Virus, and mammary tumor virus. In one embodiment, the retroviral plasmid vector is derived from Moloney Murine Leukemia Virus.

The retroviral plasmid vector is used to transduce packaging cell lines to form producer cell lines. Examples of packaging cells which maybe transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, 1: 5-14, 1990. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host. The producer cell line generates infectious retroviral vector particles that include the nucleic acid sequence(s) encoding polypeptides of the invention. Such retroviral vector particles then may be used, to transduce eukaryotic cells, either in vitro or in vivo. The transduced eukaryotic cells will express the nucleic acid sequence(s) encoding polypeptides of the invention. Eukaryotic cells that can be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

Adenoviruses and Adeno-Associated Viruses

Adenoviruses have the advantage that they have a broad host range, can infect quiescent or terminally differentiated cells, such as neurons or hepatocytes, and appear essentially non-oncogenic. See, e.g., Ali et al., 1994, at page 367. Adenoviruses do not appear to integrate into the host genome. Because they exist extrachromosomally, the risk of insertional mutagenesis is greatly reduced. Ali et al., 1994, at page 373.

Adeno-associated viruses exhibit similar advantages as adenoviral-based vectors. However, AAVs exhibit site-specific integration on human chromosome 19 (Ali et al., 1994, at page 377).

Transkaryotic Therapy

A different approach to gene therapy is "transkaryotic therapy" wherein the patient's cells are treated ex vivo to induce the dormant chromosomal genes to produce the protein of interest after reintroduction to the patient. Transkaryotic therapy assumes the individual has a normal complement of genes necessary for activation. Transkaryotic therapy involves introducing a promoter or other exogenous regulatory sequence capable of activating the nascent genes, into the chromosomal DNA of the patients' cells ex vivo, culturing and selecting for active protein-producing cells, and then reintroducing the activated cells into the patient with the intent that they then become fully established. The "gene activated" cells then manufacture the protein of interest for some significant amount of time, perhaps for as long as the life of the patient. U.S. Pat. Nos. 5,641,670 and 5,733,761 disclose in detail this concept.

In order that this invention may be better understood, the following examples are set forth. These examples are for the purpose of illustration only, and are not to be construed as limiting the scope of the invention in any manner. All patents, patent applications, and references cited in this disclosure are incorporated herein by reference in their entirety.

EXAMPLES

Example 1

Peptide Synthesis Methodology

The following general procedure was followed to synthesize some of polypeptides of the invention. Peptide synthesis was carried out by the FMOC/t-Butyl strategy (Peptide Synthesis Protocols (1994), Volume 35 by Michael W. Pennington & Ben M. Dunn) under continuous flow conditions using Rapp-Polymere PEG-Polystyrene resins (Rapp-Polymere, Tubingen, Germany). At the completion of synthesis, peptides were cleaved from the resin and de-protected using TFA/DTT/$H_2O$/Triisopropyl silane (88/5/5/2). Peptides were precipitated from the cleavage cocktail using cold diethyl ether. The precipitate was washed three times with the cold ether and then dissolved in 5% acetic acid prior to lyophilization. Peptide identity was confirmed by reversed-phase chromatography on a YMC-Pack ODS-AQ column (YMC, Inc., Wilmington, N.C.) on a Waters ALLIANCE® system (Waters Corporation, Milford, Mass.) using water/acetonitrile with 3% TFA as a gradient from 0% to 100% acetonitrile, and by MALDI mass spectrometry on a VOYAGER DE™ MALDI Mass Spectrometer, (model 5-2386-00, PerSeptive BioSystems, Framingham, Mass.). Matrix buffer (50/50 dH$_2$O/acetonitrile with 3% TFA) peptide sample was added to Matrix buffer 1/1. Those peptides not meeting the purity criteria of >95% were purified by reversed-phase chromatography on a Waters Delta Prep 4000 HPLC system (Waters Corporation, Milford, Mass.).

Example 2

Peptide Cloning

To establish a robust method for expressing polypeptides of the invention and mutants thereof, nucleotide sequences encoding polypeptides were cloned C-terminal to GST with a single Factor Xa recognition site separating the monomeric peptide and GST. The gene encoding the Factor Xa recognition site fused to the DNA sequence of the peptide to be produced has been synthesized by hybridizing two overlapping single-stranded DNA fragments (70-90mers) containing a BamHI or EcoRI restriction enzyme site immediately 5' to the DNA sequence of the polynucleotide to be cloned, followed by DNA synthesis of the opposite strands via the large fragment of DNA polymerase I (Life Technologies, Inc., Gaithersburg, Md.).

The DNA sequence chosen for each polynucleotide was based on the reverse translation of the designed amino acid sequence of each peptide. In some cases, the polynucleotide encoding the peptide is generated by PCR mutagenesis (Picard et al., *Nucleic Acids Res* 22: 2587-91, 1994; Sambrook et al. (1989) MOLECULAR CLONING: A LABORATORY MANUAL, 2nd ed., Cold Spring Harbor Laboratory Press, New York) of a polynucleotide already made by the method described above. The double-stranded product is then digested by BamHI and EcoRI and ligated into pGEX-6P-1 (Amersham Pharmacia Biotech) which has also been cleaved by BamHI and EcoRI.

For example, when the DNA sequence the polypeptide identified as SEQ ID NO:7 was cloned into pGEX-6P-1, the following polypeptide sequence was expressed as fusions with glutathione S-transferase (GST): IEGRHSQGTFTSDY-AKYLDARRAKEFIAWLVKGRG (SEQ ID NO:33), where the first 4 amino acids, IEGR, is the factor Xa recognition site and the remaining 31 amino acids is the amino acid sequence identified as SEQ ID NO:7.

The first and last six nucleotides of the nucleic acid sequence encoding the polypeptide identified as SEQ ID NO:7 represent the restriction enzyme sites (BamHI and EcoRI) used for cloning into the pGEX6P-1 plasmid (FIG. 1). The "TAATGA" sequence immediately preceding the EcoRI site ("GAATTC") encodes two stop codons. The rest of the DNA sequence encodes the Factor Xa-polypeptide identified as SEQ ID NO:7 fusion sequence.

Example 3

Peptide Recombinant Expression and Purification

BL21 (DE3) cells (Stratagene) transformed with a GST-peptide fusion containing plasmids were grown at 37° C. until OD$_{600}$ reached 0.6 to 1.0 and induced by 1 mM IPTG (Life Technologies) for 2 hours at 37° C. Two liters of cells were spun at 7,700×g for 15 minutes, and stored at −20° C. The cell pellet was resuspended in 80 ml B-PER bacterial protein extraction reagent (Cat No. 78248, Pierce) and 1× Complete Protease Inhibitor (Roche) until the cell suspension was homogenous. The homogenous mixture was gently shaken at room temperature for 10 minutes. Lysosome and Dnase I were added to a final concentration of 200 μg/ml and 10 μg/ml to further solubilize proteins and to reduce viscosity, respectively. The mixture was incubated for an additional 5 minutes. Cellular debris was spun down at 27,000 g for 20 minutes. The supernatant was mixed with 2 mL of pre-washed Glutathione Sepharose 4B resin (Pharmacia) on a shaker overnight at 4° C. The resin was spun down at 1,500 g for 15 minutes, packed into empty Poly-Prep Chromatography Columns (Bio-Rad), washed with 30 mL PBS followed by 10 mL of Factor Xa buffer (1 mM CaCl$_2$, 100 mM NaCl, and 50 mM Tris-HCl, pH 8.0). The peptides were cleaved off the column with 60 units of Factor Xa (Pharmacia) in 1 mL of Factor Xa buffer, overnight at 4° C. These eluants were then run on a C$_{18}$ HPLC (Beckman System Gold), using a 2 mL loop and flow rate of 1 mL/min with the following program: 5 minutes of Buffer A (0.1% TFA/H$_2$O), 30 minutes of gradient to 100% Buffer B (0.1% TFA/ACN), 10 minutes of Buffer A, 10 minutes of gradient, and 10 minutes of Buffer A. Peak fractions (0.5 mL each) were collected and screened by 10-20% Tricine-SDS gel electrophoresis. The identity of each peptide was confirmed by mass spectrometry using the mass predicted from the amino acid sequence. Typical yields are approximately 50 μg free peptides per liter of *E. coli* culture. Recombinant peptides have been shown to have the same activities as their synthetic versions.

The following table, Table 2, contains some selected polypeptides made according to the peptide synthesis protocol discussed above (Example 1), or recombinantly as described above.

TABLE 2

| | |
|---|---|
| Glucagon | HSQGTFTSDYSKYLDSRRAQDFVQWLMNT (SEQ ID NO:1) |
| GLP-1 (7-36) | HAEGTFTSDVSSYLEGQAAKEFIAWLVKGR-NH2 (SEQ ID NO:2) |
| GLP-1 (7-37) | HAEGTFTSDVSSYLEGQAAKEFIAWLVKGRG (SEQ ID NO:3) |
| G1 | HSQGTFTSDYSKYLDSRRAQDFVQWLVKGR-NH2 (SEQ ID NO:4) |
| G5 | HSQGTFTSDYSKYLEGQAAKEFIAWLVKGR-NH2 (SEQ ID NO:5) |
| G27 | HSQGTFTSDYAKYLDARRAKEFIAWLVKGR-NH2 (SEQ ID NO:6) |
| G51 | HSQGTFTSDYAKYLDARRAKEFIAWLVKGRG (SEQ ID NO:7) |
| G55 | HSQGTFTSDYARYLDARRAKEFIAWLVKGR-NH2 (SEQ ID NO:8) |
| G56 | HSQGTFTSDYAAYLDARRAKEFIAWLVKGR-NH2 (SEQ ID NO:9) |

TABLE 2-continued

| | |
|---|---|
| G57 | HSQGTFTSDYAKYLDAARAKEFIAWLVKGR-NH2 (SEQ ID NO:10) |
| G58 | HSQGTFTSDYAKYLDAKKAKEFIAWLVKGRG (SEQ ID NO:11) |
| G59 | NSQGTFTSDYARYLDAKKAKEFIAWLVKGRG (SEQ ID NO:12) |
| G60 | HSQGTFTSDYAKYLDAAKAKEFIAWLVKGRG (SEQ ID NO:13) |
| G61 | HSQGTFTSDYARYLDAAKAKEFIAWLVKGRG (SEQ ID NO:14) |
| G71 | HSQGTFTSDYAKYLDARRACEFIAWLVKGRG (SEQ ID NO:15) |
| G74 | HSQGTFTSDYAKYLDARRAKEFIAWLVCGRG (SEQ ID NO:16) |
| G75 | HSQGTFTSDYAKYLDARRAKEFIAWLVKCRG (SEQ ID NO:17) |
| G76 | HSQGTFTSDYAKYLDARRAKEFIAWLVKGCG (SEQ ID NO:18) |
| G77 | HSQGTFTSDYAKYLDARRAKEFIAWLVKGRC (SEQ ID NO:19) |
| G277 | HSQGTFTSDYAKYLDARRAKEFIAWLVKGRC (22kD) (SEQ ID NO:20) |
| G82 | HSQGTFTSDYARYLDARRAKEFIAWLVRGRG (SEQ ID NO:21) |
| G83 | HSQGTFTSDYARYLDARRAREFIKWLVRGRG (SEQ ID NO:22) |
| G84 | HSQGTFTSDYARYLDARRAREFIAWLVKGRG (SEQ ID NO:23) |
| G85 | HSQGTFTSDYARYLDARRAREFIAWLVRGRGK (SEQ ID NO:24) |
| G185 | HSQGTFTSDYARYLDARRAREFIKWLVRGRC (SEQ ID NO:25) |
| G2185 | HSQGTFTSDYARYLDARRAREFIKWLVRGRC (22kD) (SEQ ID NO:26) |
| G4185 | HSQGTFTSDYARYLDARRAREFIKWLVRGRC (43kD) (SEQ ID NO:27) |
| G87 | HSQGTFTSDYAKYLDARRAK(FA)EFIAWLVKGR-NH2 (SEQ ID NO:28) |
| G88 | HSQGTFTSDYAKYLDARRAKEFIAWLVKGRK(FA) (SEQ ID NO:29) |
| G90 | HSQGTFTSDYARYLDARRAREFIK(FA)WLVRGRG (SEQ ID NO:30) |
| G182 | HSQGTFTSDYARYLDARRAREFIKWLVRGRGK(FA) (SEQ ID NO:31) |
| G183 | HSQGTFTSDYARYLDARRAK(FA)EFIKWLVRGRG (SEQ ID NO:32) |

(FA): $C_{16}$ palmitate linked to the lysine residue.
(22kD): 22kD PEG linked to the cysteine residue.
(43kD): 43kD PEG linked to the cysteine residue.

Example 4

Preparation of RINm5F Cell Membranes

Flasks of RINm5F cells were washed with PBS, scraped in 20 mM Hepes-1 mM EDTA-250 mM sucrose buffer containing protease inhibitors (HES) and homogenized in a dounce homogenizer followed by repeated resuspension through a 23 gauge needle. Unbroken cells and nuclei were removed by centrifugation at 500×g for 5 minutes. The pellet was resuspended in HES buffer using a 23 gauge needle and the centrifugation was repeated. The supernatants from the two spins were combined and centrifuged at 40,000×g for 20 min. The resulting plasma membrane pellet was resuspended in HES buffer using a 23 gauge needle followed by a 25 gauge needle. Membranes were stored at −80° C. until use.

Example 5

Preparation of Plasma Membranes from Rat Liver

Rats were sacrificed and livers removed into ice cold TES buffer (20 mM Tris, pH 7.5, 1 mM EDTA, 255 mM sucrose containing protease inhibitors). The wet weight of the livers was determined and the tissue minced in 5 volumes of ice cold TES buffer and a slurry prepared using a polytron. All buffers and spins were kept at 4° C. The slurry was further homogenized using three strokes of a handheld dounce homogenizer. The homogenate was passed through several layers of cheesecloth and spun at 25,000×g for 10 minutes. Pellets were homogenized in 22.1 ml TES buffer using 10 strokes of a handheld dounce homogenizer. Twenty-seven point nine milliliters of 2.4 M sucrose in TE was added and mixed well. The homogenate was distributed among several tubes, and each tube was overlaid with 7 ml of TES buffer. The tubes were spun at 120,000×g for 60 minutes. The plasma membranes were removed from the interface that formed during the spin, diluted in TES and concentrated using a 15 minute spin at 200,000×g. The resulting pellet was again homogenized in 9.8 ml TES buffer, combined with 10.3 ml 2.4M sucrose, overlaid with 7 ml TES, and centrifuged at 180,000×g for 30 min. The plasma membranes were removed from the interface, diluted with TES buffer, and collected by centrifugation at 200,000×g for 15 min. The final pellet was resuspended in TES. Plasma membranes were stored at −80° C. until ready for use.

Example 6

Preparation of Rat Hepatocytes

Hepatocytes were isolated according to a modified procedure of Berry and Friend (*J. Cell. Biol.* 43:506, 1969). A fed male Wistar rat was anesthetized with sodium pentobarbital (55 mg/kg, i.p.). The rat was placed on its back on the tray of the liver perfusion apparatus (37° C.), and its limbs were secured with laboratory tape. The ventrical surface was cleaned with 70% alcohol, and the abdominal cavity was opened with scissors to expose the liver, portal vein, hepatic artery and the posterior vena cava. Ligatures were placed loosely around the three vessels. A cannula was inserted into the portal vein and was secured with the ligature. The hepatic artery and the posterior vena cava below the liver were tied off with the ligatures. The perfusion pump was turned on and the descending aorta was immediately severed to allow the buffer to escape and to exsanguinate the rat. The chest cavity was quickly opened to expose the heart. A cannula was inserted into the superior vena cava through the heart and was secured with a ligature to the complete the circulation of buffer through the liver. The liver was perfused with Krebs-Henseleit buffer containing 5-10% sheep RBC and under constant 95% $O_2$/5% $CO_2$ flow in situ at a flow rate of 14 ml/minute. It was perfused in a non-circulating system for 5 min and then followed by a re-circulating system (with 30 mg collagenase) for another 30 minutes. The liver was then removed, minced with scissors in a plastic beaker and filtered through a nylon sieve. The hepatocytes were separated from debris by a series of buffer washings and centrifugations (690 rpm, room temperature, 90 sec). An aliquot of cells was diluted with buffer, stained with 0.4% Trypan Blue and counted. The rest of the cells were diluted with buffer to a density appropriate for each assay.

Example 7

Protocol for Rat Islet Isolation

Sprague Dawley rats (275-320 g) were used as the source of donor islets. Briefly, the pancreas was filled with 10 ml of cold reconstituted Liberase RI (Boehringer Manheim), harvested and incubated with additional 5 ml enzyme solution in water bath for 30 minutes. Tissue suspension was washed twice with cold 10% FBS/Hanks buffer (Gibco), resuspended in 8 ml 25% ficoll (Sigma) and then layered with 5 ml each of 23%, 20% and 11% ficoll. The islets in the 20% layer after centrifugation were removed, washed twice with cold 10% FBS/Hank buffer and resuspended in 10% FBS/RPMI 1640 media (Sigma).

Example 8

Competitive Binding of Peptide to the GLP-1 Receptor in RINm5F Cell Plasma Membranes $IC_{50}$ values for the competitive binding of polypeptides and polypeptide fragments, variants, and analogs of the invention to the GLP-1 receptor in RINm5F membranes typically are at least about 0.01 nM up to about 20 nM (i.e., 0.01, 0.1 1, 2, 3, 4, 5, 6, 7, 8, 9, 10, 11, 12, 13, 14, 15, 16, 17, 18, 19, or 20 nM). $IC_{50}$ values for polypeptide derivatives of the invention typically are at least 0.01 nM up to about 500 nM (i.e., 0.01, 0.1, 1, 10, 50, 100, 150, 200, 250, 300, 350, 400, 450, or 500 nM).

Competitive binding of some polypeptides of the invention to RINm5F cell plasma membranes was measured as follows. Ninety-six-well GF/C filtration plates (Millipore, Bedford, Mass.) were blocked with 0.3% PEI for at least one hour and washed twice with binding buffer consisting of 20 mM Tris, 2 mM EDTA, pH 7.5, 1 mg/ml BSA, and 1 mg/ml bacitracin. Five micrograms of RINm5F cell plasma membranes diluted in binding buffer were applied to each well together with 0.05 µCi $^{125}I$ labeled GLP-1 and peptide concentrations ranging from $1\times10^{-12}$ to $1\times10^{-5}$ M. Following a 60 minute incubation at room temperature, the plates were washed 3 times with ice-cold PBS containing 1 mg/ml BSA. The plates were dried, scintillant was added to each well, and cpm per well determined using a Wallac Microbeta counter.

The number of $^{125}I$ counts bound to the membranes at each concentration of peptide were plotted and analyzed by non-linear regression using Prizm software to determine the $IC_{50}$. The polypeptides disclosed in Table 2 bound to the GLP-1 receptor present in the plasma membranes isolated from RINm5F cells with $IC_{50}$ values of between 1.4 nM and 248 nM (determined from a minimum of three trials). $IC_{50}$ is the concentration of a polypeptide at which maximal binding of labeled GLP-1 (7-36) (SEQ ID NO:2) is reduced by 50%.

Example 9

Competitive Binding of Peptide to the Glucagon Receptor in Rat Liver Plasma Membranes $IC_{50}$ values for the competitive binding of polypeptides and polypeptide fragments, derivatives, variants, and analogs of the invention to the glucagon receptor in rat liver membranes typically are at least about 0.1 nM up to about 1000 nM (i.e., 0.1 1, 10, 50, 100, 150, 200, 250, 300, 350, 400, 450, 500, 550, 600, 650, 700, 750, 800, 850, 900, 950, or 1000 nM).

Competitive binding of some polypeptides of the invention to rat liver plasma membranes was measured as follows. Ninety-six-well GF/C filtration plates (Millipore, Bedford, Mass.) were blocked with 0.1% PEI for at least one hour and washed twice with binding buffer consisting of 20 mM Tris, 2 mM EDTA, pH 7.5, 1 mg/ml BSA, and 1 mg/ml bacitracin. Three micrograms of rat liver plasma membranes diluted in binding buffer were applied per well together with 0.05 µCi $^{125}I$ labeled glucagon and peptide concentrations ranging from $1\times10^{-12}$ to $1\times10^{-5}$ M. Following a 60 minute incubation at room temperature, the plates were washed 3 times with ice-cold PBS containing 1 mg/ml BSA. The plates were dried, scintillant was added to each well, and cpm per well determined using a Wallac Microbeta counter.

The number of $^{125}I$ counts bound to the membranes at each concentration of peptide were plotted and analyzed by non-linear regression using Prizm software to determine the $IC_{50}$. The polypeptides disclosed in Table 2 bound to the glucagon receptor present in the plasma membranes isolated from rat liver with $IC_{50}$ values of between 11.7 nM and 726 nM (determined from a minimum of three trials). $IC_{50}$ is the concentration of a polypeptide at which maximal binding of labeled glucagon is reduced by 50%.

Example 10

Measurement of Peptide Signaling Through GLP-1 Receptor Using Cyclic AMP Scintillation Proximity Assay (SPA)

For polypeptides and polypeptide fragments, variants, and analogs of the invention, "activation" of the GLP-1 receptor in a cAMP scintillation proximity assay is induction of a maximal activity that is at least about 80% up to about 200% (i.e., 85, 90, 95, 100, 105, 110, 115, 120, 125, 130, 135, 140, 145, 150, 155, 160, 165, 170, 175, 180, 185, 190, 195, or 200%) of the maximal activity induced by the native GLP-1

(7-36) (SEQ ID NO:2) with a relative potency of at least 4% up to about 1000% (i.e., 4, 5, 10, 20, 30, 40, 50, 60, 70, 80, 90, 100, 200, 300, 400, 500, 600, 700, 800, 900, or 1000%). For polypeptide derivatives of the invention, "activation" of the GLP-1 receptor in a cAMP scintillation proximity assay is induction of a maximal activity that is at least about 80% up to about 200% (i.e., 80, 85, 90, 95, 100, 105, 110, 115, 120, 125, 130, 135, 140, 145, 150, 155, 160, 165, 170, 175, 180, 185, 190, 195, or 200%) of the maximal activity induced by the native GLP-1(7-36) (SEQ ID NO:2) with a relative potency of at least 0.5% up to about 1000% (i.e., 0.5, 1, 10, 50, 100, 200, 300, 400, 500, 600, 700, 800, 900, or 1000%). "Relative potency" is the $EC_{50}$ of native GLP-1(7-36) (SEQ ID NO:2) divided by the $EC_{50}$ of a polypeptide of the invention, multiplied by 100. "$EC_{50}$" is the concentration of a polypeptide at which 50% of the maximal activity is achieved.

Peptide signaling of GLP-1 receptor for some polypeptides of the invention using cAMP scintillation proximity assay was measured as follows. RINm5F cells were plated in 96-well plates (Costar) at $1.5 \times 10^5$ cells/well and grown at 37° C. for 24 hours in RPMI 1640, 5% FBS, antibiotic/antimycotic (Gibco BRL). The media was removed and the cells were washed twice with PBS. The cells were incubated with peptide concentrations ranging from $1 \times 10^{-12}$ to $1 \times 10^{-5}$ M in Hepes-PBS containing 1% BSA and 100 µM IBMX for 15 min at 37° C. For assay of peptides conjugated with fatty acid, the BSA was omitted from the incubation buffer. The incubation buffer was removed, and the cells were lysed in the lysis reagent provided with the cAMP Scintillation Proximity Assay (SPA) direct screening assay system (Amersham Pharmacia Biotech Inc, Piscataway, N.J.). The amount of cAMP (in pmol) present in the lysates was determined following instructions provided with this kit.

The amount of cAMP (in pmol) produced at each concentration of peptide was plotted and analyzed by nonlinear regression using Prizm software to determine the $EC_{50}$ for each peptide. The average relative potency value for GLP-1 receptor activation for the polypeptides disclosed in Table 2 was between 0.6% and 76.1%. The maximum activity induced ranged from 83% to 132% of the native peptide GLP-1(7-36) (SEQ ID NO:2) (determined from a minimum of three trials). See Table 4.

Example 11

Measurement of Peptide Signaling Through Glucagon Receptor Using Cyclic AMP Scintillation Proximity Assay (SPA)

For polypeptides and polypeptide fragments, variants, and analogs of the invention, "activation" of the glucagon receptor in a cAMP scintillation proximity assay is induction of a maximal activity that is at least about 0% up to about 75% (i.e., 0, 10 20, 25, 30, 35, 40, 45, 50, 55, 60, 65, 70, or 75%) of the maximal activity induced by the native glucagon (SEQ ID NO:1) with a relative potency from at least about 0.001 to about 5% (i.e., 0.001, 0.01, 0.1, 1, 2, 3, 4, or 5%). For polypeptide derivatives of the invention, "activation" of the glucagon receptor in a cAMP scintillation proximity assay is induction of a maximal activity that is at least about 0% to about 40% (i.e., 0, 1, 10, 20, 30, or 40%) of the maximal activity induced by the native glucagon (SEQ ID NO:1) with a relative potency of at least about 0.001 to about 1% (i.e., 0.001, 0.01, 0.1, 0.2, 0.3, 0.4, 0.5, 0.6, 0.7, 0.8, 0.9, or 1%). "Relative potency" is the $EC_{50}$ of native glucagon (SEQ ID NO:1) divided by the $EC_{50}$ of a polypeptide of the invention, multiplied by 100. "$EC_{50}$" is the concentration of a polypeptide at which 50% of the maximal activity is achieved.

Peptide signaling of glucagon receptor for some polypeptides of the invention using cAMP scintillation proximity assay was measured as follows. Freshly isolated rat hepatocytes were plated in 96 well plates at $7.5 \times 10^4$ or $2 \times 10^5$ cells/well in Hepes-bicarbonate-PBS containing 1% BSA and 100 µM IBMX. Following equilibration at 37° C. in a 5% $CO_2$/95% $O_2$ environment for 10 min, peptide at concentrations ranging from $1 \times 10^{-12}$ to $1 \times 10^{-5}$ M was added for an additional 15 min. The plates were centrifuged briefly, the incubation buffer was removed, and the cells were lysed in lysis reagent provided with the cAMP Scintillation Proximity Assay (SPA) direct screening assay system (Amersham Pharmacia Biotech Inc, Piscataway, N.J.).

The amount of cAMP (in pmol) present in the lysate was determined following instructions provided with this kit. The amount of cAMP (in pmol) produced at each concentration of peptide was plotted and analyzed by nonlinear regression using Prizm software to determine the $EC_{50}$ for each peptide. The average relative potency value (ratio of the glucagon concentration to polypeptide concentration at 50% response ($EC_{50}$)×100, determined from a minimum of three trials) for glucagon receptor activation for polypeptides of the invention was <5%. The maximum activity induced ranged from 28.3% to 71.3% of the native peptide glucagon (determined from a minimum of three trials).

The ability of the hybrid peptide to inhibit glucagon activity was measured as follows: Following equilibration at 37° C. in a 5% $CO_2$/95% $O_2$ environment for 10 min, 10 µM peptide was added to the cells followed immediately by a submaximal concentration of glucagon for 15 min. The cells were lysed and cAMP determined as described above.

After subtracting the amount of cAMP produced in the unstimulated hepatocytes from each data point, the percent inhibition was calculated as follows: Percent inhibition is the amount of cAMP produced in the presence of submaximal glucagon alone less the amount of cAMP produced in the presence of submaximal glucagon and 10 µM peptide, divided by the amount of cAMP produced in the presence of submaximal glucagon alone and multiplied by 100. The average percent inhibition of glucagon activity by the polypeptides disclosed in Table 2 was between 11.3% and 59% (determined from a minimum of three trials). See Table 4.

Example 12

Measurement of Glucose Release from Rat Hepatocytes

Inhibition of glucagon-mediated glucose production as measured by glucose release from rat hepatocytes is typically at least about 20% inhibition to about 100% inhibition (i.e., 20, 30, 40, 50, 60, 70, 80, 90, or 100%).

Inhibition of glucagon mediated glucose production by some polypeptides of the invention was measured as follows. Rat hepatocytes were added into a flat bottom 96 well plate ($2 \times 10^5$/100 µl/well) and pre-incubated in a 37° C. incubator with constant shaking and under 95% $O_2$/5% $CO_2$ flow for 10 minutes. Hepatocytes were incubated for another 30 minutes after addition of glucagon with or without peptide. Cells were then lysed with 15% perchloric acid and plates were spun at 2600 rpm, 4° C. for 15 min. The supernatant was neutralized with 1M Tris-HCl (pH 8.0): 2.5 N KOH (45:55) and spun again. The resulting supernatant was analyzed for glucose with hexokinase and glucose-6-phosphate dehydrogenase (Methods of Enzymatic Analysis, H. U. Bermeyer, Ed., Academic Press) and the $A_{340}$ read on a FMAX plate reader (Molecular Devices, Sunnyvale, Calif.).

Glucose output was calculated after subtracting the amount of glucose produced in the unstimulated hepatocytes from each data point and the percent inhibition was calculated. Percent inhibition is the amount of glucose produced in the presence of 1 nM glucagon alone less the amount of glucose produced in the presence of 1 nM glucagon and 100 nM peptide, divided by the amount of glucose produced in the presence of 1 nM glucagon alone and multiplied by 100. The polypeptide having the amino acid sequence shown in SEQ ID NO:6 inhibited glucagon mediated glucose production by 47% as determined from 3 trials. See Table 2.

Example 13

Measurement of Insulin Secretion by Perfused Rat Islets

Increase of insulin secretion by perfused rat islets in this assay is an increase of at least 1.5-fold. The GLP-1 receptor agonist component of polypeptides of the invention increases insulin secretion from perfused islets by at least 1.5-fold to about 10-fold (i.e., 1.5, 2.0, 3.0, 4.0, 5.0, 6.0, 7.0, 8.0, 9.0, or 10-fold).

Insulin secretion of perfused rat islets mediated by some peptides of the invention was measured as follows. The biphasic responses of insulin release stimulated by these polypeptides were tested by islet perfusion. Fifty islets were loaded in the perifusion chamber and perifused with HEPES-KRB containing 3 mM glucose at 37° C. After 60 min, islets were exposed to buffer containing 8 mM glucose with or without peptide (50 nM) and perifused for another 30 min. Fractions of perifusate were collected at 1 or 5 minute intervals for insulin determination. Insulin was measured using an ELISA kit (Alpco Diagnostics, Windham, N.H.). At a concentration of 50 nM, the polypeptide having the amino acid sequence shown in SEQ ID NO:6 increased insulin secretion from perfused islets approximately 2-fold, which is equivalent to that achieved by 50 nM GLP-1.

Example 14

Insulin Secretion from Dispersed Rat Islet Cells

Increase of insulin secretion from dispersed rat islet cells, in this assay, is an increase of at least 1.5-fold. The GLP-1 receptor agonist component of such polypeptides of the invention increases insulin secretion from dispersed islet cells by at least 1.5-fold to about 10-fold (i.e., 1.5, 2.0, 3.0, 4.0, 5.0, 6.0, 7.0, 8.0, 9.0, or 10-fold).

Insulin secretion of dispersed rat islets mediated by a number of peptides of the invention was measured as follows. Islets of Langerhans were isolated from SD rats (200-250 g) through a digestion procedure using collagenase. Dispersed islet cells were prepared through treatment with trypsin, seeded into 96 V-bottom plates and pelleted. Cells were cultured overnight in media. Media was aspirated and the cells were pre-incubated with Krebs-Ringer-HEPES buffer containing 3 mM glucose for 30 minutes at 37° C. Pre-incubation buffer was removed and cells were stimulated with Krebs-Ringer-HEPES buffer containing the appropriate glucose concentration (e.g., 8 mM), with and without peptides for an appropriate time at 37° C. In some studies, an appropriate concentration of GLP-1 also is included. A portion of supernatant was removed and its insulin content was measured by SPA. The results are expressed as fold over control (FOC). At a concentration of 50 nM, the polypeptide having an amino acid sequence shown in SEQ ID NO:27 increased insulin secretion from dispersed islet cells approximately 3-fold. See Table 2.

Example 15

Measuring Glucagon-Stimulated Glucose Production in Fed Wistar Rats

Inhibition of glucagon-stimulated glucose production in this assay is an inhibition of at least 20%. The glucagon receptor antagonist component of polypeptides of the invention inhibits glucagon-mediated elevation in blood glucose as measured by glucagon stimulated glucose production in fed Wistar rats is at least 20% inhibition to about 100% inhibition (i.e., 20, 30, 40, 50, 60, 70, 80, 90, or 100%).

Glucagon stimulated glucose production in fed Wistar rats by some polypeptides of the invention was measured as follows. Male Wistar rats were briefly anesthetized with isoflurane gas, tail bled for blood glucose using a Glucometer, and then given an injection into the tail vein of either vehicle (0.9% saline+1% human albumin), 0.29 nmol/kg glucagon, 1 nmol/kg polypeptides of the invention or glucagon+polypeptides of the invention. The anesthesia was withdrawn and the conscious rats were tail-bled again after 10, 20 and 30 min.

Glucose inhibition was determined by analyzing the area under the glucose curve after subtracting the basal glucose level (dAUC). Percent inhibition is defined as the amount of glucose produced by 0.3 nmol/kg glucagon alone less the amount of glucose produced by 0.3 nmol/kg glucagon in the presence of 1 nmol/kg hybrid peptide, divided by the amount of glucose produced by 0.3 nmol/kg glucagon alone and multiplied by 100.

Glucagon alone elevated blood glucose levels whereas polypeptides of the invention alone had no effect on blood glucose levels. The polypeptide having the amino acid sequence shown in SEQ ID NO:6 inhibited glucagon-mediated elevation in blood glucose by 63%. See Table 2.

Example 16

Measuring Glucagon-Stimulated Glucose Production in Fed Balb/C Mice

Inhibition of glucose production in this assay is an inhibition of at least about 20%. Preferably, the glucagon receptor antagonist component of polypeptides of the invention inhibits glucagon-mediated elevation in blood glucose in mice as measured by glucagon-stimulated glucose production in fed Balb/C mice by about 20% to about 100%, (i.e., 20, 30, 40, 50, 60, 70, 80, 90, or 100%).

Glucagon stimulated glucose production in fed Balb/C mice by some polypeptides of the invention was measured as follows. Fed male Balb/C mice were given vehicle (0.9% saline+1% human albumin) or 100 µg/kg derivatized polypeptide by subcutaneous injection 17 hours prior to the glucagon challenge. The next day the mice were fasted for 2 hours before receiving an intravenous injection of 10 µg/kg glucagon or vehicle in the tail vein. The mice were tail bled for glucose using a Glucometer just prior to the glucagon injection and again 15 minutes afterward.

The change in glucose over the 15 minutes was calculated for each mouse. Then the average change in glucose in the vehicle-treated group was subtracted from the change in glucose for each mouse in the treated groups to obtain the change in glucose due to glucagon. Percent inhibition is defined as the amount of glucose produced by 10 µg/kg glucagon alone less the amount of glucose produced by 10 µg/kg glucagon in the presence of 100 µg/kg hybrid peptide, divided by the amount of glucose produced by 100 µl/kg glucagon alone and multiplied by 100. See Table 3

TABLE 3

| Group | Glucose (mg/dl) | | | | % of -Vehicle delta | 10 µg/kg Glucagon | % Inhibition |
|---|---|---|---|---|---|---|---|
| | 0 min | 15 min | Delta (15 − 0) | | | | |
| Vehicle | 92 | 108 | 16 | | | | |
| 10 µg/kg glucagon | 95 | 195 | 100 | 84 | 100 | | |
| 10 µg/kg glucagon + 100 µg polypeptide (SEQ ID NO: 27) | 75 | 150 | 75 | 59 | 69 | 31 | |

Example 17

Measuring Increases in Plasma Insulin Levels During In Vivo Glucose Tolerance Testing (IVGTT) in Fasted Wistar Rats An increase in plasma insulin levels in this assay is an increase of at least about 2-fold. Preferably, the GLP-1 receptor agonist component of polypeptides of the invention increases insulin secretion in rats as measured by an increase in plasma insulin levels during in vivo glucose tolerance testing in fasted Wistar rats by about 2-fold to about 5-fold, more preferably by about 2-fold to about 10-fold, and still more preferably by about 2-fold to about 20-fold (i.e., 2, 3, 4, 5, 6, 7, 8, 9, 10, 11, 12, 13, 14, 15, 16, 17, 18, 19, or 20-fold).

Plasma insulin levels during in vivo glucose tolerance testing in fasted Wistar rats by some polypeptides of the invention were measured as follows. Male Wistar rats were fasted overnight and then anesthetized with isoflurane gas. The rats were given a tail vein injection of 0.4 g/kg of glucose plus either vehicle (0.9% saline+1% albumin) or 1 nmol/kg GLP-1 (positive control) or 1 nmol/kg of polypeptides of the invention. The rats were eye-bled one minute later and the plasma assayed for insulin using an ELISA Kit (Alpco Diagnostics (Windham, N.H.)). At a concentration of 1 nmol/kg, the polypeptide having the amino acid sequence shown in SEQ ID NO:6 promoted insulin secretion 3-4 fold, which is equivalent to that achieved by 1 nmol/kg GLP-1. See Table 2.

Example 18

Effect of Peptides of the Invention on Intraperitoneal Glucose Tolerance Testing (IPGTT) in Rats or Mice A decrease in blood glucose levels as measured by this assay is a decrease of at least about 10%. Preferably, the GLP-1 receptor agonist component of polypeptides of the invention decreases blood glucose levels in rats or mice as measured by intraperitoneal glucose tolerance testing in rats or mice by about 10% to about 60%, more preferably by about 10% to about 80%, still more preferably by about 10% to about 100% (i.e., 10, 20, 30, 40, 50, 60, 70, 80, 90, or 100%).

Blood glucose levels during intraperitoneal glucose tolerance testing in rats or mice by some polypeptides of the invention were measured as follows. The in vivo activity of the polypeptides of the invention when administered subcutaneously was examined in rats or mice. Rats or mice fasted overnight were given a subcutaneous injection of control or peptide (100 µg/kg). Basal blood glucose was measured prior to administration of peptides or three or 17 hours after administration of derivatized peptides, and the rats or mice were given 2 g/kg of glucose intraperitoneally. Blood glucose was measured again after 15, 30 and 60 minutes in rats or 30 and 60 minutes in mice.

Peptides of the invention significantly reduced blood glucose levels relative to the vehicle following the IPGTT, with 13%-54% reduction in the glucose AUC. This demonstrates that peptides have prolonged glucose lowering activity and a prolonged half-life in vivo. GLP-1 has a very short half-life in vivo (<10 min.). The ability of the peptides of the invention to lower blood glucose 3 hours following peptide administration is a clear indication that the peptide is present in the circulation at this time point and hence has prolonged half-life relative to GLP-1.

Example 19

Peptide PEGylation

PEGylation can be performed by any method known to those skilled in the art. However, in this instance, PEGylation was performed by introducing a unique cysteine mutation into the peptide followed by PEGylating the cysteine via a stable thioether linkage between the sulfhydryl of the peptide and maleimide group of the methoxy-PEG-maleimide reagent (Inhale/Shearwater). It is preferable to introduce the unique cysteine at the C-terminus of the peptide to minimize potential reduction of activity by PEGylation.

Specifically, a 2-fold molar excess of mPEG-mal (MW 22 kD and 43 kD) reagent was added to 1 mg of peptide (e.g., SEQ ID NO:25 having a cysteine mutation at the C-terminus of the peptide) and dissolved in reaction buffer at pH 6 (0.1M Na phosphate/0.1M NaCl/0.1M EDTA). After 0.5 hour at room temperature, the reaction was stopped with 2-fold molar excess of DTT or free cysteine to mPEG-mal. The peptide-PEG-mal reaction mixture was applied to a cation exchange column to remove residual PEG reagents followed by gel filtration column to remove residual free peptide. The purity, mass, and number of PEGylated sites were determined by SDS-PAGE and MALDI-TOF mass spectrometry. PEGylation with a smaller PEG (e.g., a linear 22 kD PEG) will less likely reduce activity of the peptide, whereas a larger PEG (e.g., a branched 43 kD PEG) will more likely reduce activity. However, the larger PEG will increase plasma half life further so that once a week injection may be possible (Harris, et al., PEGylation: A Novel Process for Modifying *Pharmacokinetics, Clin. Pharmacokinet* 40:539-551, 2001).

Example 20

Relative Potency of GLP-1 Receptor Agonist and Glucagon Receptor Antagonist Polypeptides GLP-1 binding ($IC_{50}$ values) for polypeptides listed in Table 4 was determined as described in Example 8. Relative potency values and percent GLP-1 activity were calculated as described in Example 10. Rats or mice were dosed with 100 µg/kg peptide and 3 hours post-dosing the decrease in glucose levels were determined by intraperitoneal glucose tolerance testing (IPGTT) as described in Example 18. See Table 4.

Liver membrane binding ($IC_{50}$ values) for polypeptides listed in Table 4 were determined as described in Example 9. Percent inhibition of glucagon stimulated cAMP increase was determined as described in Example 11. Rats or mice were dosed with 100 µg/kg peptide and 17 hours post-dosing glucose levels were determined by the methods of Examples 15 and 16 and reported in Table 4. Polypeptides of the invention function as GLP-1 receptor agonists and glucagon receptor antagonists in vivo.

TABLE 4

| peptide | GLP1 | | | | Glucagon | | |
|---|---|---|---|---|---|---|---|
| | RIN IC50 (nM) | Relative Potency (%) | % GLP1 max | In vivo Decrease IpGTT AUC (%)[a] | Liver IC50 (nM) | % Inhib glucagon stimulated cAMP increase | In vivo % Decrease glucagon stimulated blood glucose[b] |
| Glucagon | | | | | 1.8 | | |
| GLP-1 | 0.4 | 100 | 100 | | | | |
| G1 | 6 | 6.9 | 112.1 | | 6.6 | | |
| G5 | 0.5 | 69.9 | 109.4 | | 243.1 | | |
| G27 | 2.2 | 13.4 | 98.1 | | 69.3 | 31 | |
| G51 | 8.2 | 58.1 | 91.2 | | 154.1 | 35.2 | |
| G55 | 9.8 | 18.6 | 115.9 | | 139.2 | 32.1 | |
| G56 | 6.6 | 37.2 | 114.8 | | 125.3 | 28.6 | |
| G57 | 14.7 | 18.3 | 132.4 | | 177.5 | 18.4 | |
| G58 | 6.9 | 76.1 | 99.0 | | 163.5 | 32.6 | |
| G59 | 2.1 | 22.7 | 101.7 | | 97.5 | 41.1 | |
| G60 | 13.8 | 22.3 | 95.7 | | 682 | 21.8 | |
| G61 | 10.6 | 12.1 | 96.0 | | 232 | 45.2 | |
| G71 | 5.8 | 4.3 | 93.3 | | 25.6 | 11.3 | |
| G74 | 4.4 | 8.4 | 88.7 | | 21.7 | 23.7 | |
| G75 | 7.7 | 6.6 | 86.1 | | 54.0 | 17.1 | |
| G76 | 10.2 | 7.7 | 85 | | 59.1 | 23.0 | |
| G77 | 8.9 | 9.5 | 92.1 | | 61.1 | 18.6 | |
| G277 | ND | 1.8 | 93.7 | 46 | 65.5 | | |
| G82 | 8.1 | 29.9 | 97.1 | | 33.6 | 30.2 | |
| G83 | 3.2 | 29.9 | 89.4 | | 28.6 | 24.7 | |
| G84 | 1.4 | 61.8 | 113.9 | | 11.7 | 25.2 | |
| G85 | 1.5 | 64.5 | 95.8 | | 16.1 | 27.9 | |
| G185 | 4.5 | 13.0 | 103.9 | | 48 | 32 | |
| G2185 | 56.1 | 6.2 | 112.7 | 44 | 347 | | |
| G4185 | 248 | 0.7 | 98.3 | 36 | 547 | | 31 |
| G87 | 98.6 | 6.1 | 100.4 | 13 | 620 | 59 | |
| G88 | 109.0 | 2.3 | 118.3 | 16 | 350 | | |
| G90 | 25.4 | 0.8 | 83.5 | 13 | 726 | | |
| G182 | 12.6 | 1.4 | 104.4 | 14 | 220 | | |
| G183 | 158.7 | 0.6 | 90.5 | 27 | 663 | | |

[a] = ipGTT in mice 3 hours post dosing with 100 µg/kg peptide
[b] = glucagon challenge in mice 17 hours post dosing with 100 µg/kg peptide
ND = not determined

---

We claim:

1. An isolated polypeptide consisting of SEQ ID NO:14, wherein said polypeptide acts as both a GLP-1 receptor agonist and a glucagon receptor antagonist.

2. A pharmaceutical composition comprising a polypeptide of claim 1 in combination with a pharmaceutically acceptable carrier.

3. A method of treating a metabolic disorder in a mammal comprising administering to the mammal a therapeutically effective amount of the polypeptide of claim 1, wherein said metabolic disorder is selected from the group consisting of: type 2 diabetes, impaired glucose tolerance, impaired fasting glucose, and obesity.

4. The method of claim 3 wherein said therapeutically effective amount ranges from about 0.1 µg/kg to about 1 mg/kg.

5. The polypeptide of claim 1, wherein said polypeptide is a PEGylated form of SEQ ID NO:14.

6. The pharmaceutical composition of claim 2, wherein said polypeptide is a PEGylated form a SEQ ID NO:14.

7. The method of claim 3, wherein said polypeptide is a PEGylated form of SEQ ID NO:14.

8. The method of claim 7, wherein said therapeutically effective amount ranges from about 0.1 µg/kg to about 1 mg/kg.

9. A method of treating a metabolic disorder in a mammal comprising administering to the mammal a therapeutically effective amount of a pharmaceutical composition of claim 6, wherein said metabolic disorder is selected from the group consisting of: type 2 diabetes, impaired glucose tolerance, impaired fasting glucose, and obesity.

* * * * *

SEQUENCE LISTING

<160> NUMBER OF SEQ ID NOS: 35

<210> SEQ ID NO 1
<211> LENGTH: 29
<212> TYPE: PRT
<213> ORGANISM: Homo sapiens

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 2
<211> LENGTH: 30
<212> TYPE: PRT
<213> ORGANISM: Homo sapiens

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

```
<210> SEQ ID NO 3
<211> LENGTH: 31
<212> TYPE: PRT
<213> ORGANISM: Homo sapiens

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 4
<211> LENGTH: 30
<212> TYPE: PRT
<213> ORGANISM: Homo sapiens
<220> FEATURE:
<221> NAME/KEY: MOD_RES
<222> LOCATION: (30)..(30)
<223> OTHER INFORMATION: AMIDATION

<400> SEQUENCE: 4

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Val Lys Gly Arg
            20                  25                  30

<210> SEQ ID NO 5
<211> LENGTH: 30
<212> TYPE: PRT
<213> ORGANISM: Homo sapiens
<220> FEATURE:
<221> NAME/KEY: MOD_RES
<222> LOCATION: (30)..(30)
<223> OTHER INFORMATION: AMIDATION

<400> SEQUENCE: 5

His Ser Gln Gly Thr Phe Thr Ser Asp Tyr Ser Lys Tyr Leu Glu Gly
1               5                   10                  15

Gln Ala Ala Lys Glu Phe Ile Ala Trp Leu Val Lys Gly Arg
            20                  25                  30

<210> SEQ ID NO 6
<211> LENGTH: 30
<212> TYPE: PRT
<213> ORGANISM: Homo sapiens
<220> FEATURE:
<221> NAME/KEY: MOD_RES
<222> LOCATION: (30)..(30)
<223> OTHER INFORMATION: AMIDATION

<400> SEQUENCE: 6

His Ser Gln Gly Thr Phe Thr Ser Asp Tyr Ala Lys Tyr Leu Asp Ala
1               5                   10                  15

Arg Arg Ala Lys Glu Phe Ile Ala Trp Leu Val Lys Gly Arg
            20                  25                  30

<210> SEQ ID NO 7
<211> LENGTH: 31
<212> TYPE: PRT
<213> ORGANISM: Homo sapiens

<400> SEQUENCE: 7

His Ser Gln Gly Thr Phe Thr Ser Asp Tyr Ala Lys Tyr Leu Asp Ala
1               5                   10                  15

Arg Arg Ala Lys Glu Phe Ile Ala Trp Leu Val Lys Gly Arg Gly
```

-continued

```
                20                  25                  30

<210> SEQ ID NO 8
<211> LENGTH: 30
<212> TYPE: PRT
<213> ORGANISM: Homo sapiens
<220> FEATURE:
<221> NAME/KEY: MOD_RES
<222> LOCATION: (30)..(30)
<223> OTHER INFORMATION: AMIDATION

<400> SEQUENCE: 8

His Ser Gln Gly Thr Phe Thr Ser Asp Tyr Ala Arg Tyr Leu Asp Ala
1               5                   10                  15

Arg Arg Ala Lys Glu Phe Ile Ala Trp Leu Val Lys Gly Arg
            20                  25                  30

<210> SEQ ID NO 9
<211> LENGTH: 30
<212> TYPE: PRT
<213> ORGANISM: Homo sapiens
<220> FEATURE:
<221> NAME/KEY: MOD_RES
<222> LOCATION: (30)..(30)
<223> OTHER INFORMATION: AMIDATION

<400> SEQUENCE: 9

His Ser Gln Gly Thr Phe Thr Ser Asp Tyr Ala Ala Tyr Leu Asp Ala
1               5                   10                  15

Arg Arg Ala Lys Glu Phe Ile Ala Trp Leu Val Lys Gly Arg
            20                  25                  30

<210> SEQ ID NO 10
<211> LENGTH: 30
<212> TYPE: PRT
<213> ORGANISM: Homo sapiens
<220> FEATURE:
<221> NAME/KEY: MOD_RES
<222> LOCATION: (30)..(30)
<223> OTHER INFORMATION: AMIDATION

<400> SEQUENCE: 10

His Ser Gln Gly Thr Phe Thr Ser Asp Tyr Ala Lys Tyr Leu Asp Ala
1               5                   10                  15

Ala Arg Ala Lys Glu Phe Ile Ala Trp Leu Val Lys Gly Arg
            20                  25                  30

<210> SEQ ID NO 11
<211> LENGTH: 31
<212> TYPE: PRT
<213> ORGANISM: Homo sapiens

<400> SEQUENCE: 11

His Ser Gln Gly Thr Phe Thr Ser Asp Tyr Ala Lys Tyr Leu Asp Ala
1               5                   10                  15

Lys Lys Ala Lys Glu Phe Ile Ala Trp Leu Val Lys Gly Arg Gly
            20                  25                  30

<210> SEQ ID NO 12
<211> LENGTH: 31
<212> TYPE: PRT
<213> ORGANISM: Homo sapiens

<400> SEQUENCE: 12

His Ser Gln Gly Thr Phe Thr Ser Asp Tyr Ala Arg Tyr Leu Asp Ala
```

```
1               5                   10                  15
Lys Lys Ala Lys Glu Phe Ile Ala Trp Leu Val Lys Gly Arg Gly
            20                  25                  30

<210> SEQ ID NO 13
<211> LENGTH: 31
<212> TYPE: PRT
<213> ORGANISM: Homo sapiens

<400> SEQUENCE: 13

His Ser Gln Gly Thr Phe Thr Ser Asp Tyr Ala Lys Tyr Leu Asp Ala
1               5                   10                  15

Ala Lys Ala Lys Glu Phe Ile Ala Trp Leu Val Lys Gly Arg Gly
            20                  25                  30

<210> SEQ ID NO 14
<211> LENGTH: 31
<212> TYPE: PRT
<213> ORGANISM: Homo sapiens

<400> SEQUENCE: 14

His Ser Gln Gly Thr Phe Thr Ser Asp Tyr Ala Arg Tyr Leu Asp Ala
1               5                   10                  15

Ala Lys Ala Lys Glu Phe Ile Ala Trp Leu Val Lys Gly Arg Gly
            20                  25                  30

<210> SEQ ID NO 15
<211> LENGTH: 31
<212> TYPE: PRT
<213> ORGANISM: Homo sapiens

<400> SEQUENCE: 15

His Ser Gln Gly Thr Phe Thr Ser Asp Tyr Ala Lys Tyr Leu Asp Ala
1               5                   10                  15

Arg Arg Ala Cys Glu Phe Ile Ala Trp Leu Val Lys Gly Arg Gly
            20                  25                  30

<210> SEQ ID NO 16
<211> LENGTH: 31
<212> TYPE: PRT
<213> ORGANISM: Homo sapiens

<400> SEQUENCE: 16

His Ser Gln Gly Thr Phe Thr Ser Asp Tyr Ala Lys Tyr Leu Asp Ala
1               5                   10                  15

Arg Arg Ala Lys Glu Phe Ile Ala Trp Leu Val Cys Gly Arg Gly
            20                  25                  30

<210> SEQ ID NO 17
<211> LENGTH: 31
<212> TYPE: PRT
<213> ORGANISM: Homo sapiens

<400> SEQUENCE: 17

His Ser Gln Gly Thr Phe Thr Ser Asp Tyr Ala Lys Tyr Leu Asp Ala
1               5                   10                  15

Arg Arg Ala Lys Glu Phe Ile Ala Trp Leu Val Lys Cys Arg Gly
            20                  25                  30

<210> SEQ ID NO 18
<211> LENGTH: 31
<212> TYPE: PRT
```

<213> ORGANISM: Homo sapiens

<400> SEQUENCE: 18

His Ser Gln Gly Thr Phe Thr Ser Asp Tyr Ala Lys Tyr Leu Asp Ala
1               5                   10                  15

Arg Arg Ala Lys Glu Phe Ile Ala Trp Leu Val Lys Gly Cys Gly
            20                  25                  30

<210> SEQ ID NO 19
<211> LENGTH: 31
<212> TYPE: PRT
<213> ORGANISM: Homo sapiens

<400> SEQUENCE: 19

His Ser Gln Gly Thr Phe Thr Ser Asp Tyr Ala Lys Tyr Leu Asp Ala
1               5                   10                  15

Arg Arg Ala Lys Glu Phe Ile Ala Trp Leu Val Lys Gly Arg Cys
            20                  25                  30

<210> SEQ ID NO 20
<211> LENGTH: 31
<212> TYPE: PRT
<213> ORGANISM: Homo sapiens
<220> FEATURE:
<221> NAME/KEY: MISC_FEATURE
<222> LOCATION: (31)..(31)
<223> OTHER INFORMATION: PEGylation

<400> SEQUENCE: 20

His Ser Gln Gly Thr Phe Thr Ser Asp Tyr Ala Lys Tyr Leu Asp Ala
1               5                   10                  15

Arg Arg Ala Lys Glu Phe Ile Ala Trp Leu Val Lys Gly Arg Cys
            20                  25                  30

<210> SEQ ID NO 21
<211> LENGTH: 31
<212> TYPE: PRT
<213> ORGANISM: Homo sapiens

<400> SEQUENCE: 21

His Ser Gln Gly Thr Phe Thr Ser Asp Tyr Ala Arg Tyr Leu Asp Ala
1               5                   10                  15

Arg Arg Ala Lys Glu Phe Ile Ala Trp Leu Val Arg Gly Arg Gly
            20                  25                  30

<210> SEQ ID NO 22
<211> LENGTH: 31
<212> TYPE: PRT
<213> ORGANISM: Homo sapiens

<400> SEQUENCE: 22

His Ser Gln Gly Thr Phe Thr Ser Asp Tyr Ala Arg Tyr Leu Asp Ala
1               5                   10                  15

Arg Arg Ala Arg Glu Phe Ile Lys Trp Leu Val Arg Gly Arg Gly
            20                  25                  30

<210> SEQ ID NO 23
<211> LENGTH: 31
<212> TYPE: PRT
<213> ORGANISM: Homo sapiens

<400> SEQUENCE: 23

His Ser Gln Gly Thr Phe Thr Ser Asp Tyr Ala Arg Tyr Leu Asp Ala

```
1               5                  10                  15
Arg Arg Ala Arg Glu Phe Ile Ala Trp Leu Val Lys Gly Arg Gly
            20                  25                  30

<210> SEQ ID NO 24
<211> LENGTH: 32
<212> TYPE: PRT
<213> ORGANISM: Homo sapiens

<400> SEQUENCE: 24

His Ser Gln Gly Thr Phe Thr Ser Asp Tyr Ala Arg Tyr Leu Asp Ala
1               5                  10                  15

Arg Arg Ala Arg Glu Phe Ile Ala Trp Leu Val Arg Gly Arg Gly Lys
            20                  25                  30

<210> SEQ ID NO 25
<211> LENGTH: 31
<212> TYPE: PRT
<213> ORGANISM: Homo sapiens

<400> SEQUENCE: 25

His Ser Gln Gly Thr Phe Thr Ser Asp Tyr Ala Arg Tyr Leu Asp Ala
1               5                  10                  15

Arg Arg Ala Arg Glu Phe Ile Lys Trp Leu Val Arg Gly Arg Cys
            20                  25                  30

<210> SEQ ID NO 26
<211> LENGTH: 31
<212> TYPE: PRT
<213> ORGANISM: Homo sapiens
<220> FEATURE:
<221> NAME/KEY: MISC_FEATURE
<222> LOCATION: (31)..(31)
<223> OTHER INFORMATION: PEGylation (22 kD)

<400> SEQUENCE: 26

His Ser Gln Gly Thr Phe Thr Ser Asp Tyr Ala Arg Tyr Leu Asp Ala
1               5                  10                  15

Arg Arg Ala Arg Glu Phe Ile Lys Trp Leu Val Arg Gly Arg Cys
            20                  25                  30

<210> SEQ ID NO 27
<211> LENGTH: 31
<212> TYPE: PRT
<213> ORGANISM: Homo sapiens
<220> FEATURE:
<221> NAME/KEY: MISC_FEATURE
<222> LOCATION: (31)..(31)
<223> OTHER INFORMATION: PEGylation (43 kD)

<400> SEQUENCE: 27

His Ser Gln Gly Thr Phe Thr Ser Asp Tyr Ala Arg Tyr Leu Asp Ala
1               5                  10                  15

Arg Arg Ala Arg Glu Phe Ile Lys Trp Leu Val Arg Gly Arg Cys
            20                  25                  30

<210> SEQ ID NO 28
<211> LENGTH: 30
<212> TYPE: PRT
<213> ORGANISM: Homo sapiens
<220> FEATURE:
<221> NAME/KEY: LIPID
<222> LOCATION: (20)..(20)
<223> OTHER INFORMATION: PALMITATE
<220> FEATURE:
```

```
<221> NAME/KEY: MOD_RES
<222> LOCATION: (30)..(30)
<223> OTHER INFORMATION: AMIDATION

<400> SEQUENCE: 28

His Ser Gln Gly Thr Phe Thr Ser Asp Tyr Ala Lys Tyr Leu Asp Ala
1               5                   10                  15
Arg Arg Ala Lys Glu Phe Ile Ala Trp Leu Val Lys Gly Arg
            20                  25                  30

<210> SEQ ID NO 29
<211> LENGTH: 31
<212> TYPE: PRT
<213> ORGANISM: Homo sapiens
<220> FEATURE:
<221> NAME/KEY: LIPID
<222> LOCATION: (31)..(31)
<223> OTHER INFORMATION: PALMITATE

<400> SEQUENCE: 29

His Ser Gln Gly Thr Phe Thr Ser Asp Tyr Ala Lys Tyr Leu Asp Ala
1               5                   10                  15
Arg Arg Ala Lys Glu Phe Ile Ala Trp Leu Val Lys Gly Arg Lys
            20                  25                  30

<210> SEQ ID NO 30
<211> LENGTH: 31
<212> TYPE: PRT
<213> ORGANISM: Homo sapiens
<220> FEATURE:
<221> NAME/KEY: LIPID
<222> LOCATION: (24)..(24)
<223> OTHER INFORMATION: PALMITATE

<400> SEQUENCE: 30

His Ser Gln Gly Thr Phe Thr Ser Asp Tyr Ala Arg Tyr Leu Asp Ala
1               5                   10                  15
Arg Arg Ala Arg Glu Phe Ile Lys Trp Leu Val Arg Gly Arg Gly
            20                  25                  30

<210> SEQ ID NO 31
<211> LENGTH: 32
<212> TYPE: PRT
<213> ORGANISM: Homo sapiens
<220> FEATURE:
<221> NAME/KEY: LIPID
<222> LOCATION: (32)..(32)
<223> OTHER INFORMATION: PALMITATE

<400> SEQUENCE: 31

His Ser Gln Gly Thr Phe Thr Ser Asp Tyr Ala Arg Tyr Leu Asp Ala
1               5                   10                  15
Arg Arg Ala Arg Glu Phe Ile Lys Trp Leu Val Arg Gly Arg Gly Lys
            20                  25                  30

<210> SEQ ID NO 32
<211> LENGTH: 31
<212> TYPE: PRT
<213> ORGANISM: Homo sapiens
<220> FEATURE:
<221> NAME/KEY: LIPID
<222> LOCATION: (24)..(24)
<223> OTHER INFORMATION: PALMITATE

<400> SEQUENCE: 32

His Ser Gln Gly Thr Phe Thr Ser Asp Tyr Ala Arg Tyr Leu Asp Ala
```

```
                                -continued 1               5               10              15
Arg Arg Ala Lys Glu Phe Ile Lys Trp Leu Val Arg Gly Arg Gly
            20              25              30

<210> SEQ ID NO 33
<211> LENGTH: 35
<212> TYPE: PRT
<213> ORGANISM: Homo sapiens

<400> SEQUENCE: 33

Ile Glu Gly Arg His Ser Gln Gly Thr Phe Thr Ser Asp Tyr Ala Lys
1               5                   10                  15

Tyr Leu Asp Ala Arg Arg Ala Lys Glu Phe Ile Ala Trp Leu Val Lys
            20                  25                  30

Gly Arg Gly
        35

<210> SEQ ID NO 34
<211> LENGTH: 31
<212> TYPE: PRT
<213> ORGANISM: Homo sapiens
<220> FEATURE:
<221> NAME/KEY: MISC_FEATURE
<222> LOCATION: (11)..(12)
<223> OTHER INFORMATION: X11 = R, G, S, A, K, or T
      X12 = K, N, R, A, S, H, or Q
<220> FEATURE:
<221> NAME/KEY: MISC_FEATURE
<222> LOCATION: (16)..(18)
<223> OTHER INFORMATION: X16 = A, F, S, W, T, H, K, R, V, I, L, M, N, Q,
      G, or Y X17 = R, A, L, M, V, Q, K, F, I, W, N, D, E, H, S, T, G,
      or Y X18 = K, R, F, I, L, Y, V, M, A, G, or H

<400> SEQUENCE: 34

His Ser Gln Gly Thr Phe Thr Ser Asp Tyr Xaa Xaa Tyr Leu Asp Xaa
1               5                   10                  15

Xaa Xaa Ala Lys Glu Phe Ile Ala Trp Leu Val Lys Gly Arg Gly
            20                  25                  30

<210> SEQ ID NO 35
<211> LENGTH: 30
<212> TYPE: PRT
<213> ORGANISM: Homo sapiens

<400> SEQUENCE: 35

His Ser Gln Gly Thr Phe Thr Ser Asp Tyr Ser Lys Tyr Leu Glu Gly
1               5                   10                  15

Gln Ala Ala Lys Glu Phe Ile Ala Trp Leu Val Lys Gly Arg
            20                  25                  30
```